(12) United States Patent
Orphanos et al.

(10) Patent No.: US 11,896,200 B2
(45) Date of Patent: Feb. 13, 2024

(54) SURGICAL INSTRUMENTS WITH REFLECTIVE MIRROR-LIKE SURFACES

(71) Applicant: Medos International Sarl, Le Locle (CH)

(72) Inventors: Stephen J. Orphanos, Bridgewater, MA (US); Kirsten H. Aarsvold, Quincy, MA (US); Brian Otrando, Cumberland, RI (US)

(73) Assignee: Medos International Sarl, Le Locle (CH)

( * ) Notice: Subject to any disclaimer, the term of this patent is extended or adjusted under 35 U.S.C. 154(b) by 30 days.

(21) Appl. No.: 17/545,579

(22) Filed: Dec. 8, 2021

(65) Prior Publication Data

US 2022/0087514 A1    Mar. 24, 2022

Related U.S. Application Data

(62) Division of application No. 15/676,293, filed on Aug. 14, 2017, now Pat. No. 11,219,355.

(51) Int. Cl.
| | |
|---|---|
| *A61B 17/34* | (2006.01) |
| *A61B 1/00* | (2006.01) |
| A61B 90/00 | (2016.01) |

(52) U.S. Cl.
CPC ...... *A61B 1/00135* (2013.01); *A61B 1/00089* (2013.01); *A61B 1/00096* (2013.01); *A61B 1/00163* (2013.01); *A61B 17/3421* (2013.01); *A61B 17/3472* (2013.01); *A61B 17/3415* (2013.01); *A61B 90/37* (2016.02); *A61B 2017/349* (2013.01); *A61B 2017/3484* (2013.01); *A61B 2090/3618* (2016.02)

(58) Field of Classification Search
CPC ............ A61B 17/3421; A61B 17/3423; A61B 1/00135; A61B 17/0218
See application file for complete search history.

(56) References Cited

U.S. PATENT DOCUMENTS

| | | | |
|---|---|---|---|
| 5,957,832 A | 9/1999 | Taylor et al. | |
| 6,017,355 A | 1/2000 | Hessel et al. | |
| 7,473,220 B2* | 1/2009 | Francese | A61B 17/3421 600/184 |
| 8,257,251 B2 | 9/2012 | Shelton, IV et al. | |
| 8,834,358 B2 | 9/2014 | Mckinley et al. | |
| 9,167,955 B2 | 10/2015 | Kucklick | |
| 9,364,248 B2* | 6/2016 | Yacoubian | A61B 17/00234 |
| 2003/0055437 A1 | 3/2003 | Yasunaga | |
| 2004/0143167 A1 | 7/2004 | Branch et al. | |
| 2007/0100210 A1 | 5/2007 | Selover et al. | |
| 2008/0045797 A1 | 2/2008 | Yasushi et al. | |
| 2009/0105546 A1 | 4/2009 | Hestad et al. | |

(Continued)

*Primary Examiner* — Si Ming Ku

(57) ABSTRACT

Systems, devices, and methods for providing a surgeon with improved viewing angles during arthroscopic surgical procedures are provided. In some embodiments, a cannula is provided that includes an elongate body that can extend along a longitudinal axis, the body having a proximal end, a distal end, a lumen extending through the body between openings at the proximal and distal ends. The cannula can have a first flange member that can extend at least partially around at least one of the openings, and the first flange member can have a distal-facing surface, where at least a portion of the distal-facing surface can be reflective.

15 Claims, 17 Drawing Sheets

(56) References Cited

U.S. PATENT DOCUMENTS

| | | |
|---|---|---|
| 2010/0261974 A1 | 10/2010 | Shelton, IV et al. |
| 2012/0029281 A1 | 2/2012 | Frassica et al. |
| 2012/0277541 A1 | 11/2012 | Bhargava et al. |
| 2012/0323081 A1 | 12/2012 | Son |
| 2013/0204095 A1 | 8/2013 | Mark et al. |
| 2014/0207084 A1 | 7/2014 | Webb et al. |
| 2016/0157842 A1 | 6/2016 | Kurzweil et al. |
| 2016/0220240 A1 | 8/2016 | Hart et al. |
| 2019/0046018 A1 | 2/2019 | Orphanos et al. |

* cited by examiner

SURGICAL INSTRUMENTS WITH REFLECTIVE MIRROR-LIKE SURFACES

CROSS REFERENCE TO RELATED APPLICATIONS

The present application is a division of U.S. patent application Ser. No. 15/676,293, now U.S. Pat. No. 11/219,355, entitled "Surgical Instruments With Reflective Mirror-Like Surfaces" filed Aug. 14, 2017, which is hereby incorporated by reference in its entirety.

FIELD

The current subject matter generally relates to a surgical instrument, such as a cannula, with a reflective mirror-like surface.

BACKGROUND

Arthroscopic surgical procedures are minimally invasive procedures that require only small incisions to access a surgical site. These minimally invasive procedures allow for less traumatic surgeries and therefore reduce patient discomfort and speed recovery. Arthroscopic surgical procedures can be used to treat a variety of injuries and conditions, such as, for example, repair of soft tissue damage or reattachment of soft tissue to bone and/or surrounding tissue. For example, when otherwise healthy tissue has been torn away from a bone, such as a shoulder labrum being partially or completely torn from a glenoid rim (a labrum tear), surgery is often required to reattach the tissue to the bone, to allow healing and natural reattachment to occur.

Despite numerous benefits of arthroscopic procedures, because the surgeries are performed within an enclosed space (e.g., an interior of a joint) that is accessed via relatively small entrance opening(s), the ability to maneuver the necessary surgical instruments, such as an arthroscope, within the joint space can be limited. Accordingly, certain areas of a surgical site may be difficult to view or may not be accessible for viewing. In this way, a surgeon may not be able to view some areas of the surgical site.

Accordingly, there is a need for improved systems and methods for visualizing a surgical site during an arthroscopic surgical procedure.

SUMMARY

In one aspect, a cannula is provided that in some embodiments includes an elongate body extending along a longitudinal axis. The body can have a proximal end, a distal end, and a lumen extending through the body between openings at the proximal and distal ends. The cannula can also include a first flange member that can extend at least partially around at least one of the openings. The first flange member can have a first surface, and at least a portion of the first can be reflective.

The cannula can vary in a number of ways. For example, the first flange member can have a circular cross-section in a plane normal to the longitudinal axis of the body. As another example, the first flange member can have a first radius of curvature.

In some implementations, the first flange member can be oriented at an angle relative to the longitudinal axis of the body from about 90 degrees to about 150 degrees. In other implementations the first flange member can be oriented at an angle relative to the longitudinal axis of the body from about 10 degrees to about 170 degrees.

As another example, an angle at which the first flange member can be oriented relative to the longitudinal axis of the body can be adjustable. The angle can be adjustable using an adjustment device that can have an inner lumen that can be configured to receive the body therein. The adjustment device can be movable along the longitudinal axis of the body to adjust the angle. In some embodiments, the angle is adjustable such that the first flange member is configured to move between a first configuration and a second configuration.

In some embodiments, the cannula can include a second flange member that can extend at least partially around another one of the openings, and the second flange member can have a second surface, wherein at least a portion of the second surface is reflective. The second flange member can be curved.

In another implementation, an outer wall of the body can have at least one thread formed thereon. In some implementations, the first flange member can be flexible. As another example, the reflective portion of the first surface can be substantially flat. As yet another example, the body can be one of flexible and rigid. In some implementations, a diameter of at least one portion of the body can vary along the longitudinal axis thereof.

In another aspect, a method is provided that in some embodiments includes advancing a cannula through a first portal to a target site in a patient's body, advancing an imaging device that can have at least one image sensor through a second portal towards the target site, performing a surgical function at the target site, and viewing a result of the surgical function with the imaging device by directing the imaging device at a reflective surface of the cannula that displays a reflected image of the result of the surgical function at the target site.

The method can vary in a number of ways. For example, the first portal can include one of an anterior portal and a posterior portal, and the second portal can include another one of the anterior portal and the posterior portal. As another example, performing the surgical function at the target site can include forming a hole in a bone.

DETAILED DESCRIPTION

Figure 1:
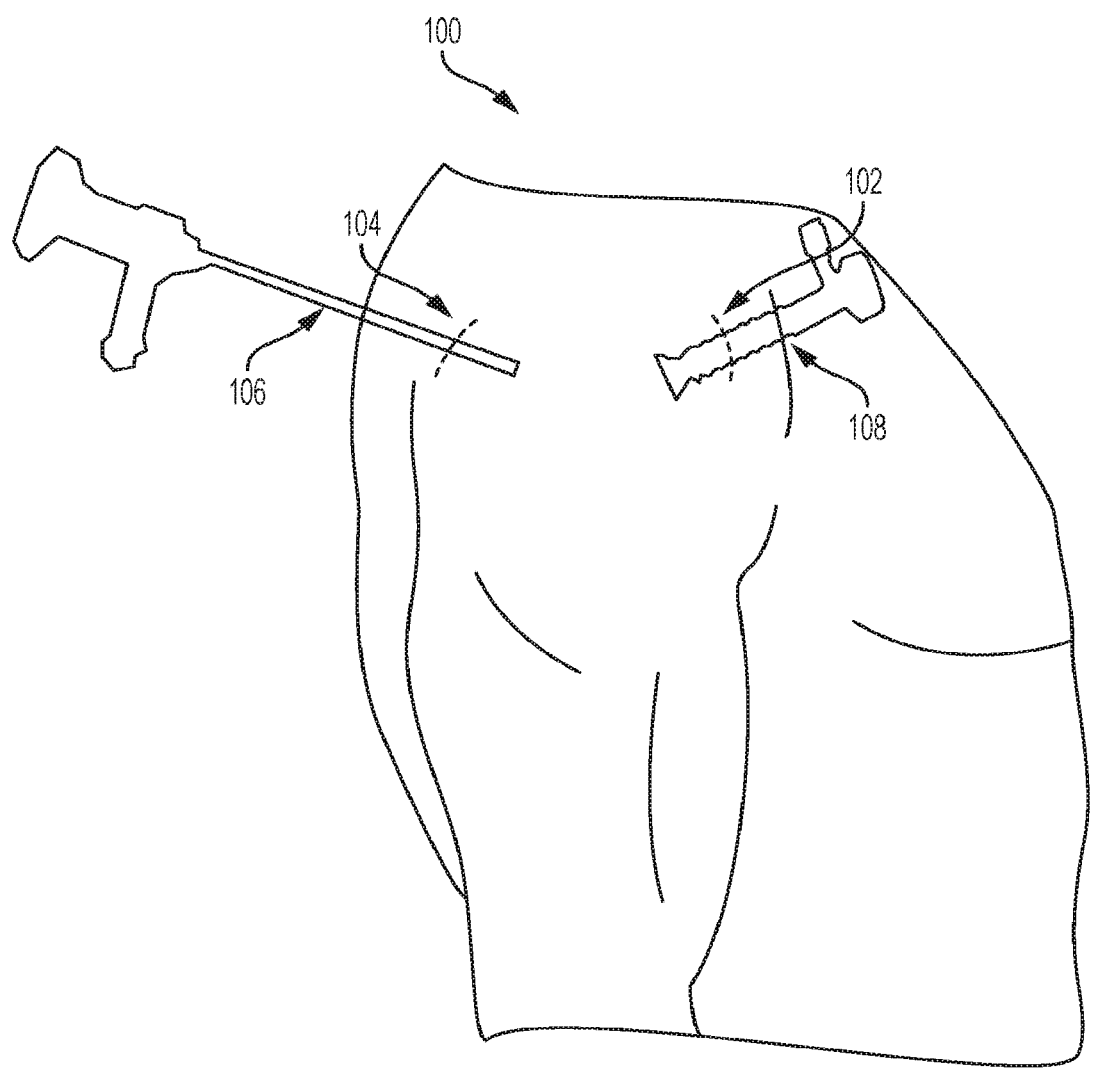
FIG. 1 is a schematic diagram example of a side view of a shoulder during a surgical procedure.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

A variety of injuries and conditions can require repair of damaged soft tissue, or reattachment of soft tissue to bone and/or surrounding tissue. For example, when otherwise healthy tissue has been torn away from a bone, such as a shoulder labrum being partially or completely torn from a glenoid rim (a type 2 labrum tear), surgery is often required to reattach the tissue to the bone to allow healing and a natural reattachment to occur.

A cannula for use in minimally invasive surgical procedures is provided. In general, the cannula includes an elongate body extending along a longitudinal axis, the body having a proximal end, a distal end, and a lumen extending through the body between openings at the proximal and distal ends. The cannula also includes a first flange member that extends at least partially around at least one of the openings. The first flange member includes a first surface, such as a distal-facing surface, wherein at least a portion of the first surface is reflective. The cannula described herein can be used in minimally invasive surgical procedures, including arthroscopic surgical procedures.

The cannula having at least one reflective surface can allow a surgeon to view areas of a surgical site that would otherwise be obscured from view. In particular, the surgeon can position an imaging device such as, e.g., an arthroscope, such that the reflective surface of the cannula is in the field of view of the imaging device and reflects a desired target area of the surgical site. The surgeon can adjust a position of the cannula, if desired. In this way, the target area of the surgical site, including a result of a surgical function that can be performed at the surgical site, is in the field of view of the imaging device and is thus visible to a surgeon operating the imaging device. This can provide improved visibility of the surgical site without the need for additional tools and/or additional access portals.

FIG. 1 shows schematically an example of a side view of a shoulder 100 during a surgical procedure. In a procedure such as a labral repair of a glenohumeral joint (GHJ), for example, a surgical site at the joint can be accessed through an anterior portal 102 and through another, posterior portal 104. In some cases, the surgeon can view the surgical site using an imaging device 106, such as, for example, an arthroscope, that can be inserted through the posterior portal 104. A cannula 108 proving access to the surgical site is inserted through the anterior portal 102. Instruments to be used to perform a surgical procedure at the surgical site can be inserted to the surgical site through the cannula 108. The arthroscope 106 can have a 30 degree viewing angle, though the arthroscope can have any other viewing angle. It should be appreciated that the surgical site at the shoulder 100 can include various instruments that are not shown for the sake of simplicity.

Due to the anatomy of a joint, such as a shoulder joint, and the viewing angle of an imaging instrument (e.g., an arthroscope), at least part of the working area may not be in the field of view of the imaging instrument. This can be a common problem not only in shoulder labral repair, but in arthroscopic procedures in general. For example, a hole in a bone (e.g., a glenoid rim) formed for insertion of a suture anchor may not be in a view of an imaging instrument used to visualize the surgical site. Thus, insertion of the suture anchor into the pre-formed bone hole can be complicated. In some cases, a surgeon may place a guide wire that can extend from the drilled hole, and the guide wire can be used to identify or "mark" the location of the hole that can later be accessed. This and other efforts to maintain visibility of a working area nevertheless tend to result in added procedural steps, and/or additional devices used, which can complicate and prolong the surgery.

During an arthroscopic shoulder labral repair procedure, while viewing a surgical site (e.g., from a posterior portal), it can be desirable and advantageous to be able to view around corners or around a glenoid rim and/or down the neck of the glenoid. Accordingly, in some embodiments, a cannula that has a reflective surface is provided that allows viewing areas of a surgical site that are otherwise not in the field of view of the imaging device being used. The cannula described herein allows the surgeon to view the surgical site by directing the imaging device at the reflective surface of the cannula that displays a reflected image of the surgical site. In this way, areas of the surgical site that may otherwise be obscured are visualized.

The cannula having at least one reflective surface can have various configurations. In one example, the cannula has a generally elongate body extending along a longitudinal axis and having a proximal end, a distal end, a lumen extending through the body between openings at the proximal and distal ends. The cannula also has a first flange member or flange that extends at least partially around at least one of the openings. The first flange has a distal-facing surface and at least a portion of the distal-facing surface is reflective. In some embodiments, the cannula can also have a second flange member or flange that extends at least partially around an opposed opening. In some implementations, a proximal-facing surface of the second flange can have at least one portion thereof that is reflective. It should be appreciated that the surface of a flange is referred to as a "distal-facing" or a "proximal-facing" to denote a direction which the surface is facing when the cannula is inserted into a portal in a patient's body. In some embodiments, for example, when a cannula has a single flange or when only one of the flanges has a reflective portion, that flange can be said to have a distal-facing reflective surface in any use of the cannula in which the flange is advanced distally into a surgical site. In implementations in which a cannula has first and second flanges at opposed ends thereof and both of the flanges have a reflective surface, the cannula can be advanced through a portal such that, depending on the cannula's orientation, either of the flanges can be distal-facing or proximal-facing.

The flange of the cannula can have various configurations. For example, it can be configured such that its distal-facing surface is convex, concave, or it can have a shape such that at least a portion thereof is convex and at least a portion thereof is concave. Also, in some implementations, the distal-facing surface can be substantially flat. In some embodiments, the cannula can include a flange that is conical. As another variation, the flange can be formed partially or entirely around an opening to a lumen of the cannula. It is also understood that the flange can be oriented at various angles relative to a longitudinal axis of a cannula's body.

In some embodiments, a diameter of at least one portion of a body of the cannula can vary along its longitudinal axis, which can facilitate manipulation of the cannula within a target site. In some embodiments, a flange of the cannula is adjustable between various configurations of its distal-facing surface to provide various viewing angles. For example, the flange can be adjustable such that it can move between concave and convex configurations.

Any one or more portions of a distal-facing surface of a flange can be reflective. The surface can be made reflective in various ways. For example, reflective portions can be created using an over-molding process. The over-molding process can involve, for example, incorporating a thin reflective member that can be made of, e.g., polycarbonate, polyurethane, or other flexible film, into a molding process to create a cannula with soft, flexible reflective surfaces. The thin reflective member can be created using another process, and then incorporated secondarily into the molding process to create the cannula. In other embodiments, surface reflectivity is achieved by adhering one or more mirrors or mirror-like components at desired location(s). Such mirrors or mirror-like components can be rigid or flexible. Mirrors can also be incorporated into the molding process with an over-mold where mirrors can be placed into a cavity where the mold is then created. As another example, surface reflectivity can be obtained by covering (e.g., painting) a portion of a cannula with a reflective material. It should be appreciated that any portion of the cannula can be reflective. For example, in some embodiments, at least a portion of a distal-facing and a proximal-facing reflective surface of the flange members can be reflective. Additionally, one or more portions of a body of the cannula can have reflective qualities to aid viewing the target site during a surgical procedure.

In some embodiments, the cannula can be flexible or rigid, or it can be at least partially flexible and/or at least partially rigid. In some embodiments, a body of the cannula can be rigid. In other embodiments, the body of the cannula can be flexible. One or more flanges can be flexible or rigid, depending on a desired application. In some cases, one of the flanges is more flexible than another. In at least one embodiment, a body of a cannula can be more rigid than at least one flange of the cannula. Rigid portions of a cannula can be made of, e.g., polycarbonate, or from any other suitable material(s). Flexible portions can be made of soft material such as, for example, silicone, Pellethane® thermoplastic polyurethane (TPU) having Shore A durometer of approximately 50-100 A, or other polyurethane material(s) with suitable Shore A durometer characteristics.

Figure 2:
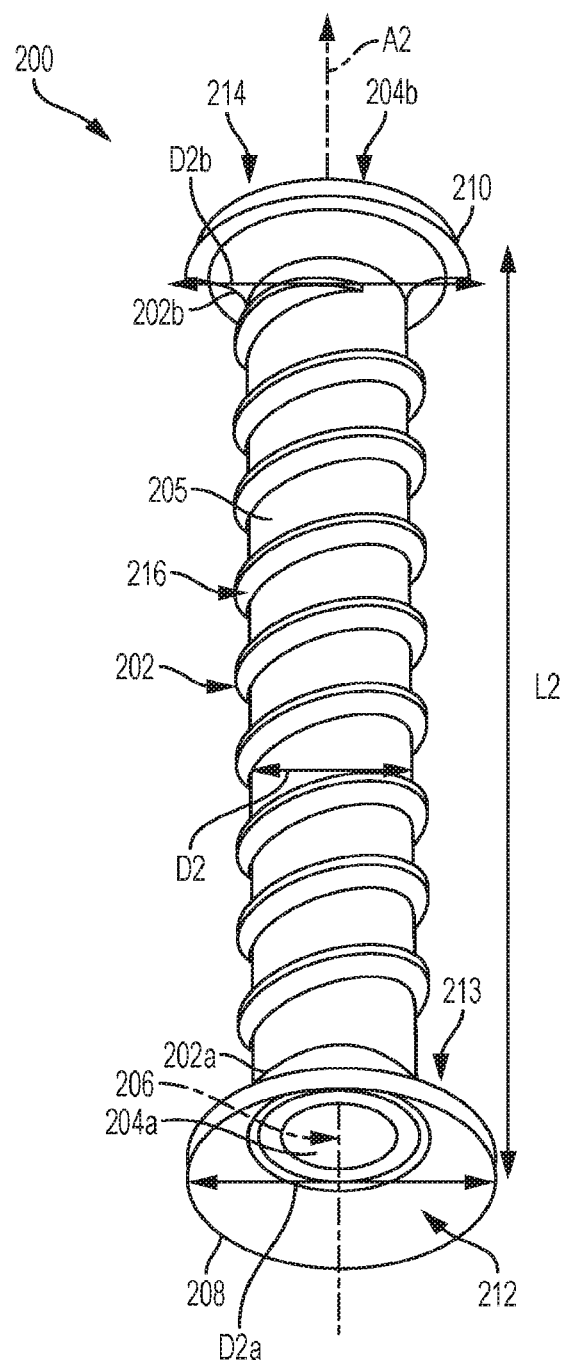
FIG. 2 is a bottom perspective view of an embodiment of a cannula.

FIG. 2 shows an embodiment of a cannula 200 that can be used in arthroscopic surgical procedures. The cannula 200 has an elongate body 202 having a longitudinal axis A2 extending between distal and proximal ends 202a, 202b of the body 202. The body 202 has a first opening 204a at the distal end 202a thereof, a second opening 204b (obscured in FIG. 1) at the proximal end 202b thereof, and a lumen 206 extending through the body 202 between the first opening 204a and the second opening 204b. As shown in FIG. 2, the cannula 200 also includes a first flange member or flange 208 that extends at least partially around the first opening 204a, and a second flange member or flange 210 that extends at least partially around the second opening 204b. It should be appreciated that, although in this example, the first and second flanges 208, 210 are shown formed around the respective first and second openings 204a, 204b such that the flanges are adjacent to the openings, in other implementations, the flanges can be formed at a distance from the openings. In such implementations, at least one of the flanges can be formed such that the flange is offset from the opening along the body of the cannula.

As shown schematically in FIG. 2, the body 202 has a diameter D2, the first flange member 208 has a diameter D2a, and the second flange member 210 has a diameter D2b. The diameters D2, D2a, D2b, as well as a length L2 of the cannula 200, can vary in any manner, for example, depending on the anatomy of a patient at a surgical site where the cannula 200 can be used, type of a surgical procedure in which the cannula is to be used, and any other factors.

As shown in FIG. 2, the first flange member 208 of the cannula 200 has a distal-facing surface 212, and at least a portion of the distal-facing surface 212 is reflective. Similarly, the second flange member 210 has a proximal-facing surface 214 (obscured in FIG. 2), and at least a portion of the proximal-facing surface 214 is reflective. As used herein, a "reflective surface" is defined as a surface that at least partially reflects incident light and is thus able to form a reflected image with enough clarity to discern details of tissue or features within the joint, such as a drilled hole. In some embodiments, a reflective surface can have a reflectivity of at least 40% for incident light at wavelength between about 390 nm and about 700 nm. The reflective surface can display the reflected image such that a surgeon viewing the reflective surface with an imaging instrument can view areas of a target site that may otherwise be beyond the reach of the imaging instrument.

In the example of FIG. 2, the first and second flange members 208, 210 have circular cross-sections in planes normal to the longitudinal axis A2 of the body 202. Depending on where the cross-section is taken along a height of each of the flanges, a diameter of the cross-section can be different. Also, in other implementations, the cross-sections of one or both of the flanges can be different from circular. In this embodiment, as also shown in FIG. 2, the flange 208 is generally dome-like or trapezoidal. In particular, the distal-facing surface 212, as viewed in a proximal direction, is concave. The opposed surface 213 of the flange 208, such as the top surface of the dome-like flange 208, is generally convex, if viewed in a distal direction. It should be appreciated that the distal-facing surface 212 of the flange 208 that faces the lumen 206 can be configured differently from the opposed, outer surface 213 of the flange 208. Furthermore, a shape of walls of the flange 208 can vary in different ways. For example, although, in this example, the flange 208 resembles a hemispherical dome with a truncated top, in other embodiments, it can have other shapes, including irregular shapes. In some embodiments, as discussed in more detail below, the shape of the reflective surface of a flange of a cannula can be such that at least a portion of the surface is substantially flat, i.e. lies in a plane normal to a longitudinal axis of a body of the cannula.

As shown in FIG. 2, an outer wall 205 of the cannula's body 202 has at least one thread 216 (or a similar surface feature) formed thereon. The thread(s) 216 aid in securing a position of the cannula within tissue. Also, in some embodiments, the threads 216 allow "zooming" of the cannula 200 such that the position of the cannula 200 can be adjusted by pushing or pulling the cannula 200 into, or out of, a joint space. Furthermore, in some embodiments, the threads 216 also function to couple the cannula 200 to another component such as a sheath or a mounting member. The at least one thread 216 can be coarse or fine, and it can have any suitable diameter and pitch. Also, any suitable number of threads can be formed on the outer wall 205 of the cannula's body 202. As another variation, the body 202 can have other surface features.

The cannula 200 can have any suitable properties and it can be made from any suitable material or a combination of materials. For example, as mentioned above, it can be flexible, rigid, or it can be at least partially flexible and/or at least partially rigid. In some embodiments, the body 202 of the cannula 200 can be flexible. A flexible body 202 can allow the cannula 200 to be deformed such that it can reach surgical sites that would otherwise be difficult or impossible to reach with a rigid body. Also, when the body of the cannula is flexible, it decreases a risk of trauma to the surgical site when the cannula is disposed in the site and manipulated in the site in a desired manner.

In some embodiments, the flanges 208, 210 of the cannula 200 can be at least partially soft and flexible such that they can bend and deform in order to be inserted into a surgical site. Flexible flange members 208, 210 can also be manipulated, deformed, and/or bent while in contact with, or in close proximity to, anatomical structures, without damaging those structures. The flange members can be flexible (e.g., resiliently flexible), such that they can be folded back or otherwise deformed for being pushed through a portal in the patient's body. Once at a target site (e.g., within a joint space), the flanges can return at least in part to the original configuration. In addition, the flanges can be manipulated at the target site so as to be positioned for viewing by an imaging device. In embodiments in which a flange member is flexible, a reflective surface of that flange member is flexible such that the reflective surface can be deformed without affecting negatively its ability to reflect anatomical structure and results of surgical functions. In other embodiments, the flanges 208, 210 of the cannula 200 can be rigid.

It should be appreciated that any portion of the cannula 200 can be reflective. For example, in some embodiments, in addition to having at least a portion of the distal-facing and proximal-facing reflective surfaces 212, 214 of the flange members 208, 210 reflective, one or more portions of the cannula's body 202 can have reflective qualities to aid in viewing the target site during a surgical procedure.

The reflective surfaces in accordance with the described techniques can be formed in a number of various ways. For example, in some embodiments, reflective portions of the distal-facing surface 212 and/or the proximal-facing surface 214 are created using a reflective film that can be placed onto the surfaces 212, 214. For example, the film can be a flexible adhesive film that can be adhered to desired portions of the cannula 200. In other embodiments, reflective portions of the distal-facing and proximal-facing surfaces 212, 214 are created via a physical vapor deposition process on one or more surfaces. Non-limiting examples of materials that can be deposited include aluminum, silver, aluminum oxide, chromium, cobalt, copper, gold, molybdenum, nickel, tin, titanium, tungsten, alloys of any of these materials, as well as any other materials.

As another example, reflective portions of the distal-facing and proximal-facing surfaces 212, 214 can be created using an over-molding process or by attaching mirror-like components, which can be rigid or flexible, onto one or more surfaces where reflectivity is desired. Mirrors can also be incorporated into the molding process. The surface reflectivity can be obtained through a painting process, or using any other suitable process.

It should be appreciated that the cannula in accordance with the described techniques, such as cannula 200 (FIG. 2), can have numerous variations. For example, in some embodiments, the cannula can include an obturator for introduction into a joint space. The obturator can be made of plastic and it can be sized so as to be compatible with the cannula. The obturator can be disposable or reusable. In some embodiments, the obturator is packaged with the cannula. As another variation, in some embodiments, in order to prevent fluids from entering a cannula's lumen during a surgical procedure, at least one of the openings of the lumen can have a sealing element that can substantially prevent fluids from entering the lumen while allowing tools to be passed therethrough. The sealing element can have various configurations. In some embodiments, for example, the sealing element extends at least partially across a respective opening of the cannula's lumen. It should be appreciated that each of the aforementioned exemplary features can apply to any of the cannulas and other surgical tools discussed herein.

Figure 3:
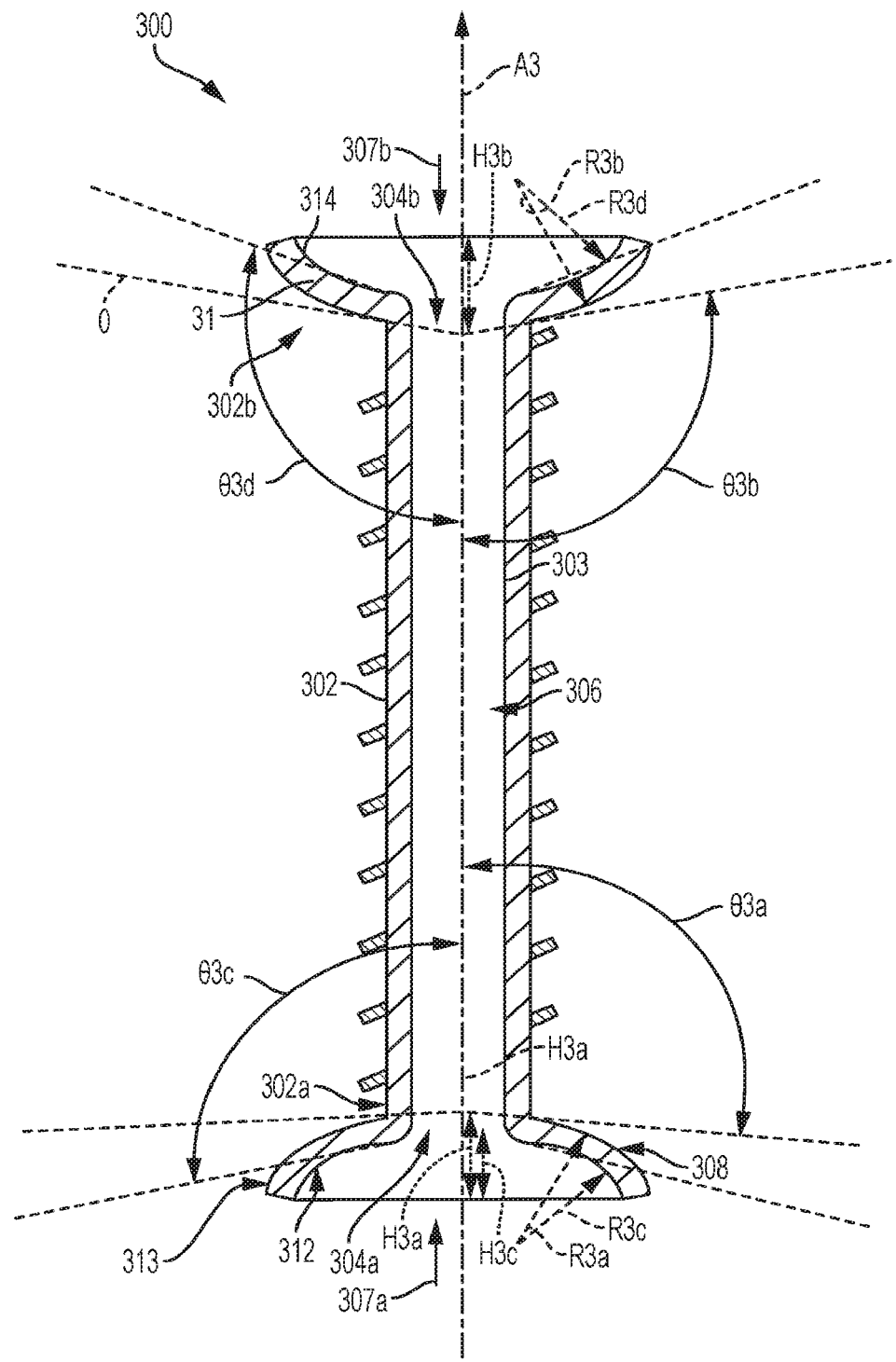
FIG. 3 is a side cross-sectional view of another embodiment of a cannula.

FIG. 3 illustrates another embodiment of a cannula 300, which is generally similar to cannula 200 of FIG. 2. As shown in FIG. 3, the cannula 300 includes an elongate body 302 having a longitudinal axis A3 extending between distal and proximal ends 302a, 302b thereof. The body 302 has a first opening 304a at the distal end 302a, a second opening 304b at the proximal end 302b, and a lumen 306 extending through the body 302 between the first and second openings 304a, 304b. As shown, the lumen 306 is defined by an interior wall 303 of the body 302. The cannula 300 also includes first and second flange members or flanges 308, 310 that extend radially outward from the distal end 302a and the proximal end 302b of the body 302, respectively. The first and second flanges 308, 310 extend around the first and second openings 304a, 304b, respectively, and have respective first and second surfaces 312, 314. Each of the first and second surfaces 312, 314 can be distal-facing or proximal-facing, depending on which of the flanges 308, 310 is inserted first into a portal in a patient's body. For example, if the cannula 300 is inserted into a portal such that the first flange 308 is inserted first and is thus closer to a surgical site (the second flange 310 in such a scenario can be disposed outside of the portal), the first surface 312 of the first flange 308 is referred to as distal-facing. At least a portion of the first surface 312 and/or the second surface 314 is reflective.

In this example, as shown in FIG. 3, the first and second flanges 308, 310 are generally dome-shaped, with the body 302 extending between the tops of the dome-like flanges 308, 310. The first and second surfaces 312, 314, which are in this example inner surfaces of the dome-like first and second flanges 308, 310, respectively, and concave. As used herein, a surface (a distal-facing or a proximal-facing) of a cannula's flange formed around a lumen's opening is defined as concave or convex depending on how that surface is seen from outside of the flange, in a direction towards the cannula's lumen. Thus, for example, the first surface 312 of the first flange 308 is concave as viewed from outside of the flange 308 towards the inside of the lumen 306, as shown by arrow 307a in FIG. 3. The second flange 310 of the cannula 300 is similarly concave as seen in a direction shown by arrow 307b in FIG. 3. Further, as shown in FIG. 3, the first flange 308 has a height H3a and the second flange 310 has a height H3b. The heights H3a, H3b are measured along a line that coincides with a centerline of the cannula's body 302. In this example, the centerline of the cannula's body 302 is defined by the longitudinal axis A3 of the cannula's body 302.

As shown in FIG. 3, each of the first and second flanges 308, 310 has an outer surface and an inner surface. As mentioned above, the flanges' inner surfaces define the first and second surfaces 312, 314, respectively. The first flange 308 is shown in FIG. 3 to have an outer surface 313. Because the flange 308 has a certain thickness, the "dome" defined by the outer surface 313 of the flange 308 has the height H3a that is greater than a height H3c of a "dome" defined the first (inner) surface 312 of the flange 308. It should be appreciated that, in this example, the height H3c of the dome-like first surface 312 of the flange 308 is measured along the same line along which the height H3a of the dome-like outer surface 313 of the flange 308 can be measured. The second flange 310 of the cannula 300 is configured similarly to the first flange 308. It should further be appreciated that, in some embodiments, the shapes of the outer surface of a flange and an inner surface of the flange (which can have at least one reflective portion) can be different.

As shown in FIG. 3, the first flange 308 has a first radius of curvature R3a, and the second flange 310 has a second radius of curvature R3b. In this example, the radii of curvature R3a, R3b can be substantially the same. Also, as shown schematically in FIG. 3, the first flange 308 is oriented at a first angle θ3a relative to the longitudinal axis A3 of the body 302, and the second flange 310 is oriented at a second angle θ3b relative to the longitudinal axis A3 of the body 302. In this example, the first and second angles θ3a, θ3b can be substantially the same—about 100°, though the angles can range between about 90° and 120°. In some embodiments, however, the first and second angles θ3a, θ3b can be different. As also shown in FIG. 3, the first surface 312 of the first flange 308 is oriented at a third angle θ3c relative to the longitudinal axis A3 of the body 302, and the second surface 314 of the second flange 310 is oriented at a fourth angle θ3d relative to the longitudinal axis A3 of the body 302. In this example, the third and fourth angles θ3c, θ3d are different from the first and second angles θ3a, θ3, and are about 110°. In some embodiments, however, the third and fourth angles θ3c, θ3d can be different.

It should be appreciated that the flanges of the cannula, as well as surfaces of the flanges that are at least partially reflective, can be oriented at various angles relative to a longitudinal axis of a cannula's body. Thus, although in the example of FIG. 3 the flanges 308, 310 and their reflective surfaces 312, 314 are disposed at obtuse angles relative to the longitudinal axis A3 of the body 302, in other embodiments, these angles can be straight or acute. For example, in various embodiments, the first, second, third, and fourth angles θ3a, θ3b, θ3c, θ3d can vary in the range from approximately 10° to approximately 170°. In other embodiments, the first, second, third, and fourth angles θ3a, θ3b, θ3c, θ3d are in the range from approximately 90° to approximately 150°.

It should also be appreciated that, in embodiments in which a flange of a cannula is at least partially flexible, the shape of the flange and of its reflective surface can change when the flange is disposed at a surgical site. For example, the flange can be at least partially deformed within the surgical site.

As shown in FIG. 3, the first surface 312 of the first flange 308 has a radius of curvature R3c and the second surface 314 of the second flange 310 has a radius of curvature R3d. In this example, the radii of curvature R3c, R3d of the surfaces 312, 314 of the flanges 308, 310 are approximately equal. In other embodiments, however, the radii of curvature R3c, R3d of the surfaces 312, 314 can be different. Different configurations can allow the surgeon to remove the cannula 300 from a portal providing access to a joint, flip the cannula, and insert the cannula's opposite end into the portal, for alternate viewing angles of the joint.

In the example shown in FIG. 3, as mentioned above, at least a portion of the first surface 312 and/or second surface 314 is reflective. A reflective surface of a concave surface of a flange, e.g., of the concave surface 312 of the first flange 308, can direct incoming light back towards the longitudinal axis A3 of the cannula 300 when the first flange 308 is inserted into a patient during a surgical procedure. This can allow a static view to be triangulated with an instrument that can be inserted down the lumen 306 of the cannula 300 towards an anatomic structure or a hole.

Figure 4:
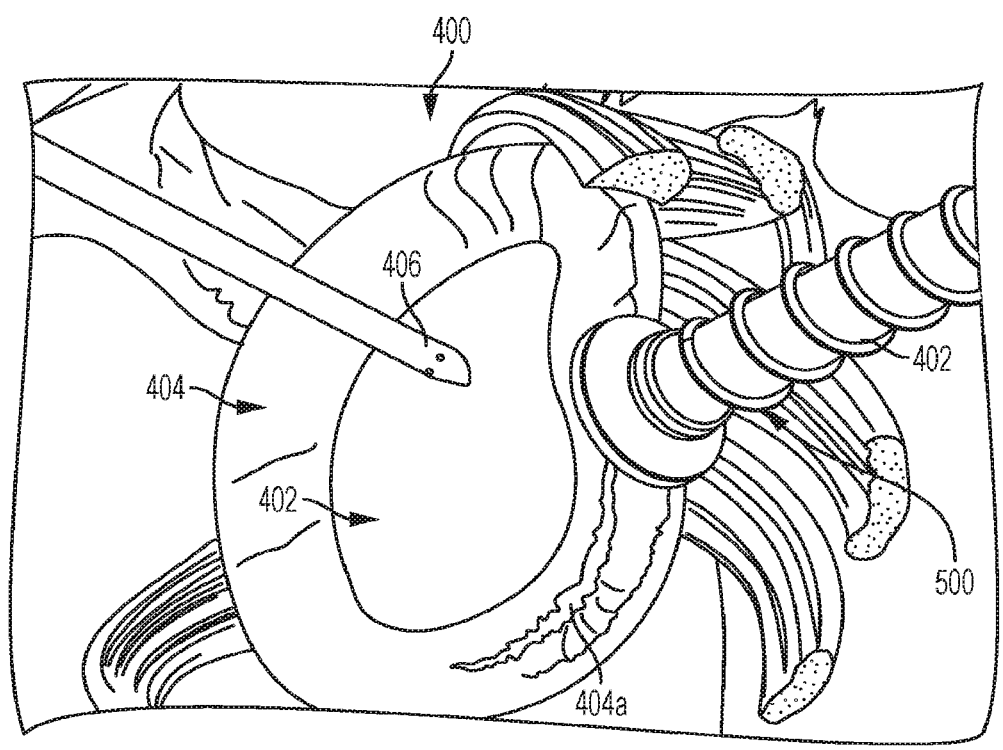
FIG. 4 is a schematic diagram of a lateral view of a glenohumeral joint (GHJ) during a labral repair procedure.
Figure 5A:
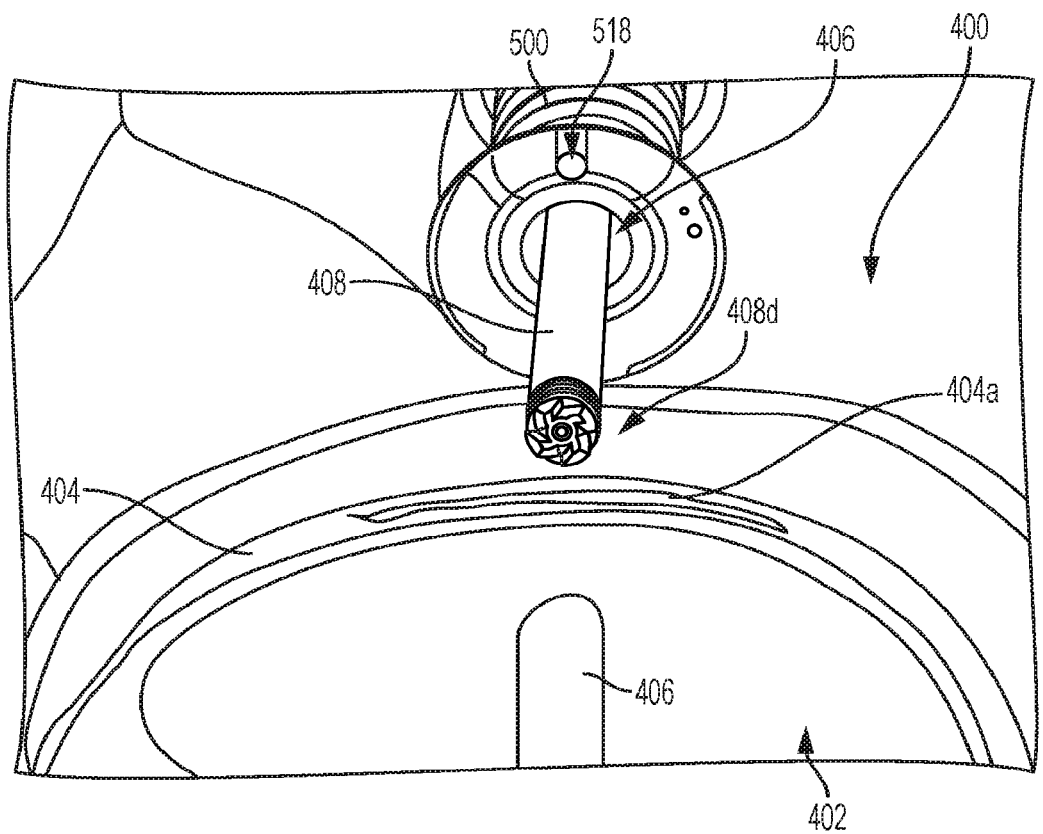
FIG. 5A a schematic diagram of a posterior view of the GHJ of FIG. 4, illustrating a surgical function being performed.
Figure 5B:
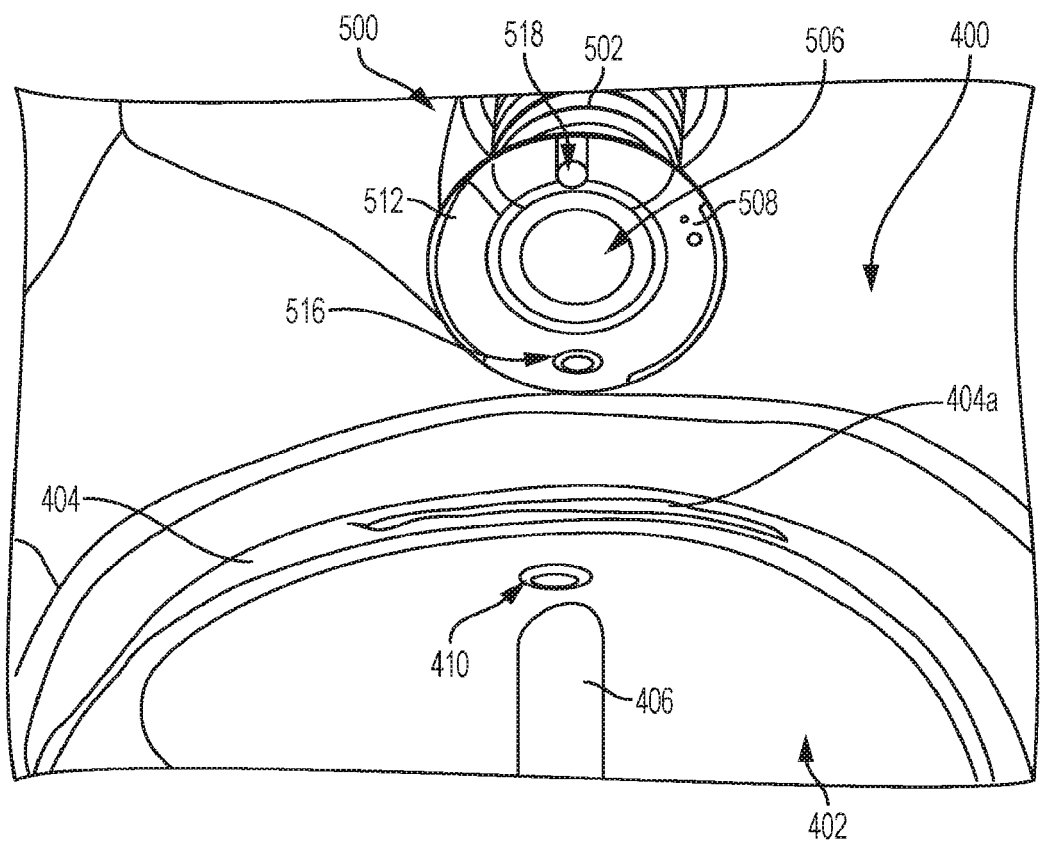
FIG. 5B is a schematic diagram of a posterior view of the GHJ of FIG. 5A, illustrating a result of the surgical function.

FIGS. 4, 5A, and 5B show an example of a surgical site 400 at a glenohumeral joint (GHJ) during a labral repair procedure. The surgical site 400 includes a glenoid 402, and a labrum 404 that has a tear 404a. In the example illustrated, a cannula 500 is inserted into the surgical site 400 at the interior of the joint via a first portal. A second portal is also created that receives an imaging device such as an arthroscope 406. The first and second portals can each be created via respective small incisions. In the illustrated embodiment, the first portal is the anterior portal, and the second portal is the posterior portal. However, it should be appreciated that, in other embodiments, the first portal can be a posterior portal and the second portal can be an anterior portal. Also, other portals can be created additionally or alternatively.

The cannula 500 is shown by way of example as generally similar to cannula 200 (FIG. 2) and cannula 300 (FIG. 3), though the cannula 500 can have other configurations. As shown in FIGS. 5A and 5B, the cannula 500 includes a body 502 having a lumen 506 extending therethrough, and a first flange member 508 that has a reflective distal-facing surface 512. The arthroscope 406 can be any suitable elongated instrument that allows a surgeon to illuminate and view at least a portion of the surgical site 400 at the joint space.

In use, a cannula is advanced through a first portal to a target site in a patient's body. An imaging device, such as an arthroscope, having at least one image sensor is advanced through a second portal toward the target site. When the arthroscope and the cannula are at the surgical site, the surgeon performs a surgical function at the target site. For example, some labral repair procedures involve drilling a hole in a glenoid rim to provide anchor points to reattach the labrum 404. FIGS. 5A and 5B illustrate a portion of the surgical site 400 at the GHJ as seen from a posterior direction. While working through the anterior portal through which the cannula 500 is inserted, the surgeon places a drill guide on the glenoid rim, and then proceed to drill a hole at some angle to the glenoid rim. FIG. 5A shows a drill bit 408 having its distal end 408d extending through the lumen 506 of the cannula 500 towards the surgical site 400. The drill bit 408 can be used to form a hole in the glenoid 410, and FIG. 5B shows the hole 410 that has been drilled in the glenoid 402. Once the hole 410 has been formed, an implant, such as a suture anchor, can be inserted into the hole 410 through the anterior portal.

Due to a limited visibility of a surgical site, during an arthroscopic surgical procedure, a surgeon typically needs to rely on his/her experience to manually examine various areas at the surgical site until there is a tactile feedback of the implant being inserted into a hole formed in the bone. From the posterior viewing position, looking anteriorly with an arthroscope, the surgeon may not be able to view the hole that has been formed once a drill guide is removed from the joint space. In some cases, prior to removing the drill guide, a guide wire can be inserted into the drilled hole. However, even though, with the use of the guide wire, a trajectory to the hole may be visible, the imaging device still may not be able to view the hole itself or structures covering the hole, such as tissue or other anatomical features. Because of the limited ability of the imaging device to view the joint space, insertion of an implant into a hole can be complicated.

Accordingly, the techniques described herein provide improved visualization of a surgical site, such as a joint space. In particular, the cannula used to access the surgical site and to pass surgical instruments therethrough has a reflective surface that allows an imaging device to view areas that otherwise would be obscured. Thus, the surgeon can view a result of a surgical function performed at a target surgical site, with an imaging device (e.g., an arthroscope) by directing the imaging device at a reflective surface of the cannula that displays a reflected image of the result of the surgical function at the target site.

Referring back to FIG. 5A, from the posterior viewing position, looking in the anterior direction with the arthroscope 406, the surgeon may not be able to see a result of a surgical function performed at the target surgical site because the hole 410 (shown in FIG. 5B) is outside of the field of vision of the arthroscope 406. In the illustrated embodiment, directing a light source of the arthroscope 406 onto the reflective surface of the cannula 500 provides a reflected image at the reflective surface of the cannula 500 and the image can be viewed by the arthroscope 406. The position of the cannula 500 can be adjusted to provide a desired view of the surgical site such that the reflective surface 512 of the cannula 500 displays a reflected image 516 of the hole 410, as shown in FIG. 5B. The position of the arthroscope 406 can also be adjusted, if desired, to position the arthroscope 406 such that a reflection of features of interest at the surgical site (e.g., the hole 410) is in the field of view of the arthroscope 406. In this way, the hole 410, which can be formed on the glenoid rim on in another area that can be obscured from the view of the arthroscope 406, can be visualized. The cannula 500 and the arthroscope 406 are positioned such that the reflective distal-facing surface 512 is in the field of view of the arthroscope such that the hole 410 is visible in the reflected image 516. This allows the surgeon to view the hole 410 after it has been drilled, which simplifies placing the implant into the hole 410. The surgeon can also perform other steps of the surgery, which can be facilitated by the improved view of the surgical field, including the hole 410 and other features. For example, the surgeon can remove any soft tissue surrounding the hole 410 by introducing a shaver or another tool suitable for the task, clean up the surgical area, and then place the implant directly into the hole 410.

As shown in FIGS. 5A and 5B, in this example, the reflective surface 512 of the cannula 500 can also display a reflected image 518 of a distal end of the arthroscope 406. However, in some embodiments, a reflected image of the distal end of the arthroscope may not be displayed on a reflective surface of the cannula, or the reflected image of the distal end of the arthroscope can be displayed at certain positions of the cannula.

Figure 6:
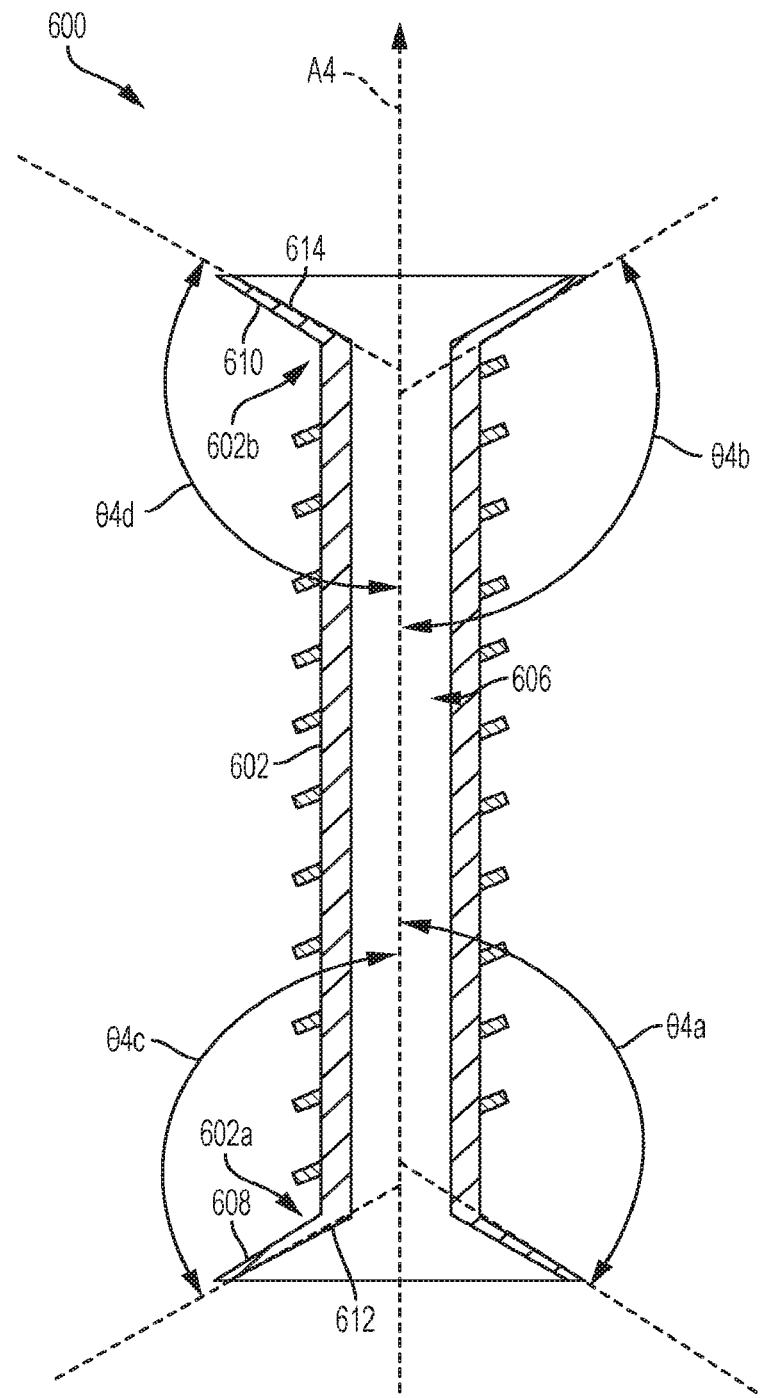
FIG. 6 is a side cross-sectional view of yet another embodiment of a cannula.

As mentioned above, a cannula having at least one reflective portion can have various configurations, including various configurations of its flanges. For example, in some embodiments, a cannula includes at least one flange member that is conical. FIG. 6 shows an embodiment of a cannula 600 that is generally similar to cannula 300 (FIG. 3), but it includes first and second flange members or flanges 608, 610 that are generally conical. In this example, each of the first and second flanges 608, 610 is a right circular cone (i.e. its base is circular) with a truncated apex. However, one or both of the flanges 608, 610 can be configured as a cone with an oval base. Also, in some implementations, one or both of the flanges 608, 610 can be shaped as angled cones.

Similar to the description above with respect to cannula 300 (FIG. 3), the cannula 600 has a body 602 having a longitudinal axis A4 and a lumen 606 extending through the body 602 between distal and proximal ends 602a, 602b thereof. Flanges 608, 610 extend radially outward from the distal and proximal ends 602a, 602b of the body 602, respectively. As shown in FIG. 6, the flanges 608, 610 are oriented at first and second angles θ4a, θ4b, respectively, relative to the longitudinal axis A4 of the body 602. In this example, the first and second angles θ4a, θ4b are substantially the same.

The first and second flanges 608, 610 include respective first and second surfaces 612, 614, at least a portion of each of which is reflective. At least a portion of the first surface 612 is oriented at a third angle θ4c relative to the longitudinal axis A4 of the body 602, and at least a portion of the second surface 614 is oriented at a fourth angle θ4d relative to the longitudinal axis A4 of the body 602. In this example, the third and fourth angles θ4c, θ4d are substantially the same.

Figure 7:
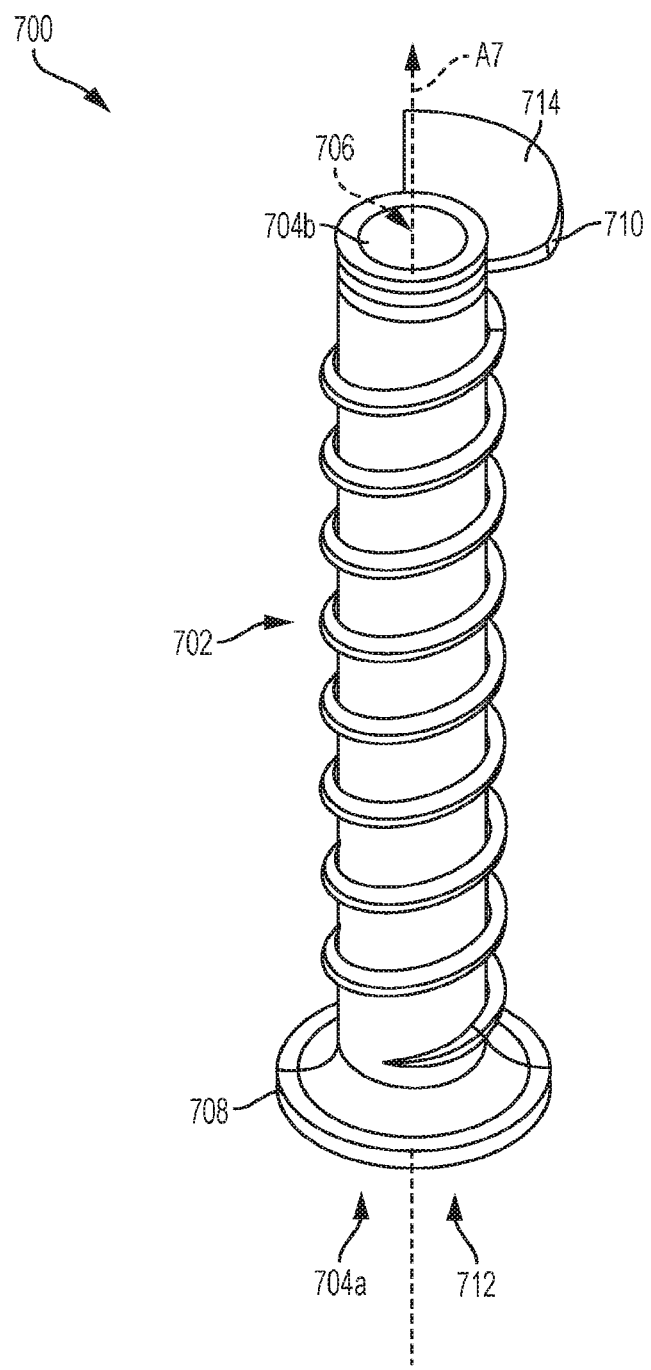
FIG. 7 is a top perspective view of an embodiment of a cannula that has a flange member that extends partially around an opening.
Figure 8:
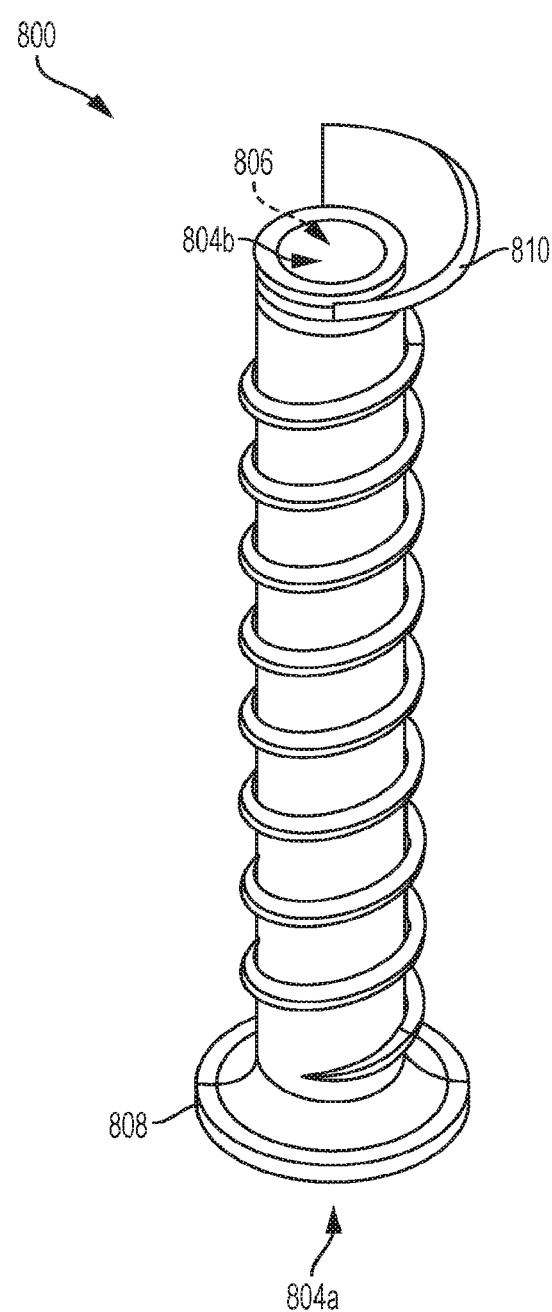
FIG. 8 is a top perspective view of another embodiment of a cannula that has a flange that extends partially around an opening.

In some embodiment, at least one flange of a cannula extends partially around a respective opening in a body of the cannula, rather than around the entire circumference of the opening. FIGS. 7 and 8 show cannulas 700, 800, respectively, that each has a flange extending partially around an opening leading into a lumen in the cannula.

As shown in FIG. 7, the cannula 700 includes a body 702 having a longitudinal axis A7 and a lumen 706 extending between a first opening 704a and a second opening 704b. The cannula 700 is generally similar to cannulas 200, 300, 600 described above with respect to FIGS. 2, 3, and 6, respectively. In this embodiment, however, the cannula 700 includes a first flange member 708 that extends around the entire first opening 704a, and a second flange member 710 that extends partially around the second opening 704b. In the illustrated example, the second flange member 710 extends around approximately one quarter of the second opening 704b, though such flange can extend around any portion of the second opening, the portion being smaller than the entire circumference of the second opening. As also shown in FIG. 7, the first and second flange members 708, 710 have first and second surfaces 712, 714, respectively. As in the other examples described herein, at least a portion of the first 712 and/or the second surface 714 is reflective.

FIG. 8 similarly shows a cannula 800 having a flange that extends only partially around a respective opening. In particular, while a first flange member 808 of the cannula 800 extends around the entire circumference of a first opening 804a into a lumen 806 of the cannula 800, a second, opposed flange member 810 extends partially around a second opening 804b of the lumen 806. In the illustrated example, the second flange member 810 extends around approximately a half of the circumference of the second opening 804b.

Figure 9:
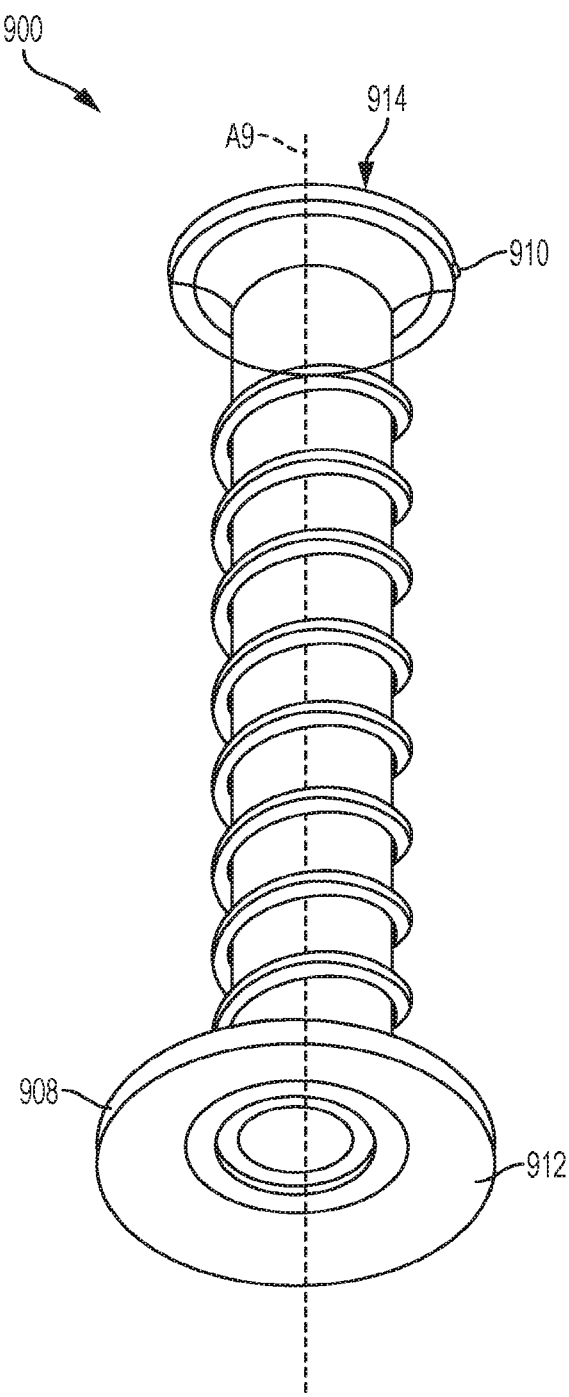
FIG. 9 is a bottom perspective view of an embodiment of a cannula having a flange with a substantially flat reflective surface.

In some embodiments, a cannula has a flange member with a substantially flat reflective surface. FIG. 9 shows a cannula 900 that is generally similar to cannula 300 (FIG. 3), but the cannula 900 includes first and second flanges 908, 910 at least one of which has a substantially flat reflective surface that is substantially perpendicular to a longitudinal axis A9 of the cannula 900. The term "substantially" is defined herein as largely but not necessarily wholly what is specified (and includes what is specified; e.g., substantially flat includes flat), as understood by a person of ordinary skill in the art. As shown, the first flange 908 has a first reflective surface 912 that is substantially flat. A second reflective surface 914 of the second flange 910 can also be substantially flat. In this example, the cannula 300 is configured such that at least the first flange 908 has the flat reflective surface 912 in the original configuration of the cannula 300. In some implementations, the first flange 908 can be resiliently flexible such that it can change its shape while the cannula 300 is passed through a surgical portal and then revert to the original shape once the flange 908 is at a surgical site. It should be appreciated that the cannula 300 having the flange with a substantially flat reflective surface can have features as described in connection with any of the embodiments described herein. For example, the flange can be formed partially around the opening of an inner lumen of the cannula, the cannula can be associated with an adjustment mechanism configured to cause the flange to change its shape, etc. Also, although in this example the entire surface 912 of the flange 908 is reflective, in other embodiments, the reflective surface 912 can be partially reflective.

Figure 10:
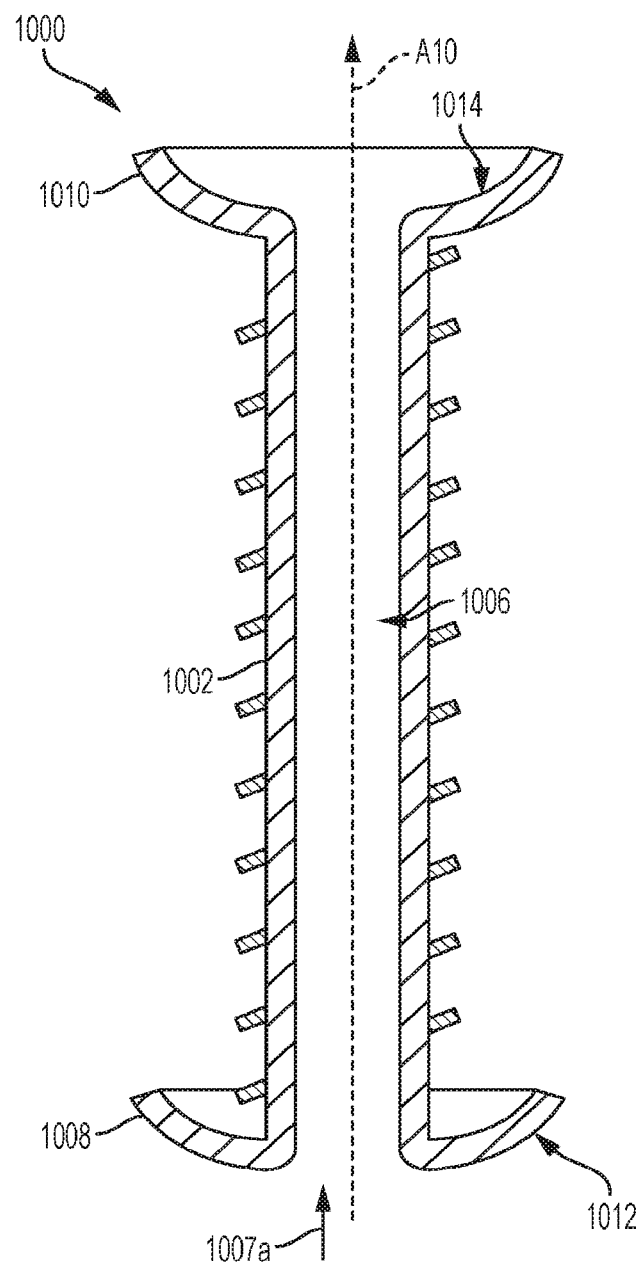
FIG. 10 is a cross-sectional view of an embodiment of a cannula that has a convex flange member.

In some implementations, a cannula can have a flange member that has a convex surface. FIG. 10 shows an example of a cannula 1000 that has a body 1002 with a longitudinal axis A10, and a lumen 1006 extending through the body 1002. The cannula 1000 is generally similar to cannula 200 (FIG. 2) and cannula 300 (FIG. 3). However, in this example, the cannula 1000 has a first flange 1008 that is generally convex, as viewed in a direction shown by an arrow 1007a in FIG. 10—from the outside of the flange 1008 towards the lumen 1006. A first surface 1012 of the first flange 1008 is thus also generally convex as viewed from the direction indicated by the arrow 1007a. As shown in FIG. 10, a second flange 1010 of the cannula 1000 having a second surface 1014 is generally concave. At least a portion of each the first and second surfaces 1012, 1014 is reflective. As in the other embodiments described herein, the first and second surfaces 1012, 1014 can face distally towards a surgical site in a joint or proximally towards a surgeon operating the cannula, depending on which end of the cannula 1000 is advanced distally into the surgical site.

The convex configurations of the first flange 1008 and the first surface 1012 of the flange 1008 provide a surgeon with alternate viewing angles as compared to those provided by a concave surface. Reflective portions of the first surface 1012 are outward-facing that direct incoming light away from the longitudinal axis A10. Reflective portions of the second surface 1014 of the second flange 1010 are inward-facing such that the reflective portions can direct incoming light back towards the longitudinal axis A10 of the cannula 1000.

In some circumstances, it can be beneficial to be able to adjust a configuration of one or more flanges of a cannula. Adjustment of the cannula's flange allows adjusting a surface of the flange, at least a portion of which is reflective. In this way, the cannula can be positioned at a surgical site in a desired manner and/or in a manner that allows altering a viewing angle provided by a reflective surface of the flange member. Thus, in some embodiments, a flange of a cannula can be adjustable such that it can selectively move between a first configuration and a second configuration. For example, a flange, and therefore its reflective surface, can move between concave and convex configurations to provide different viewing angles. Also, in some embodiments, the flange can be configured to move between two or more discrete configurations, while in other embodiments the flange can be continuously adjustable such that it can have varying configurations.

The flange can be moved between different configurations in various ways. For example, in some embodiments, the cannula includes an adjustment device, such as a sheath, that can be slidably disposed over a body of the cannula. A portion of the sheath, which can be removable, is coupled to the flange such that when the flange is moved in a proximal direction, the flange can be moved from a concave configuration to a convex configuration. Also, the flange can move between various intermediate configurations.

Figure 11A:
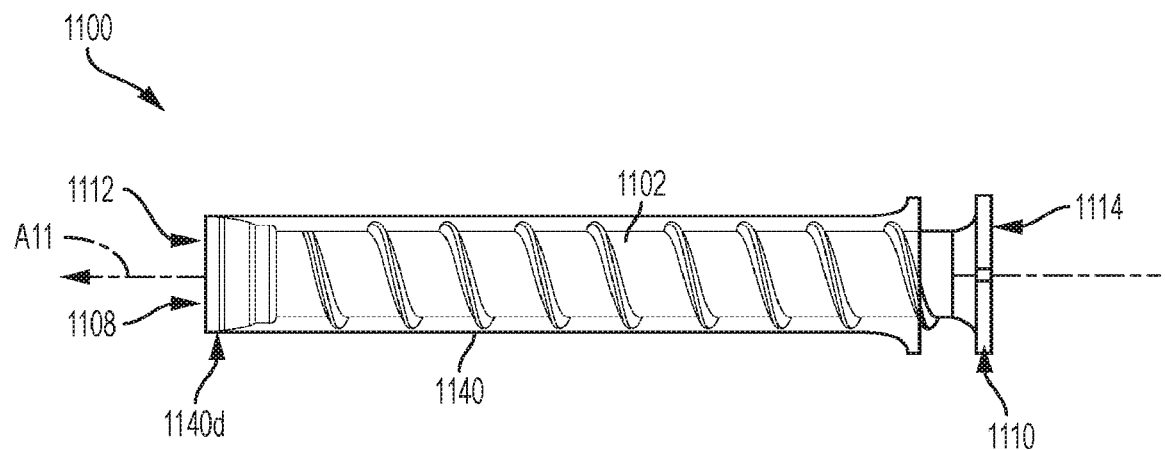
FIG. 11A is a side view of a cannula having a flange that is adjustable, where the flange member is shown in a first position.
Figure 11B:
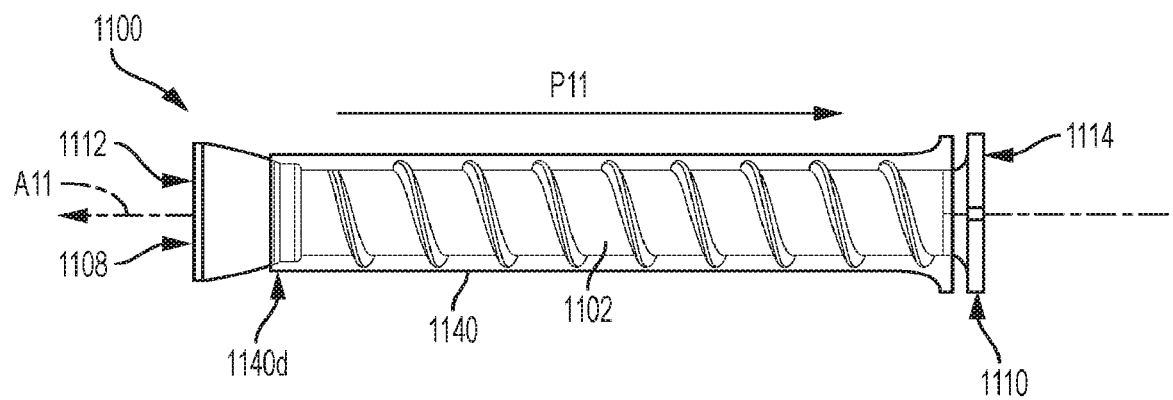
FIG. 11B is a side view of the cannula of FIG. 11A, where the flange is shown in a second position.
Figure 11C:
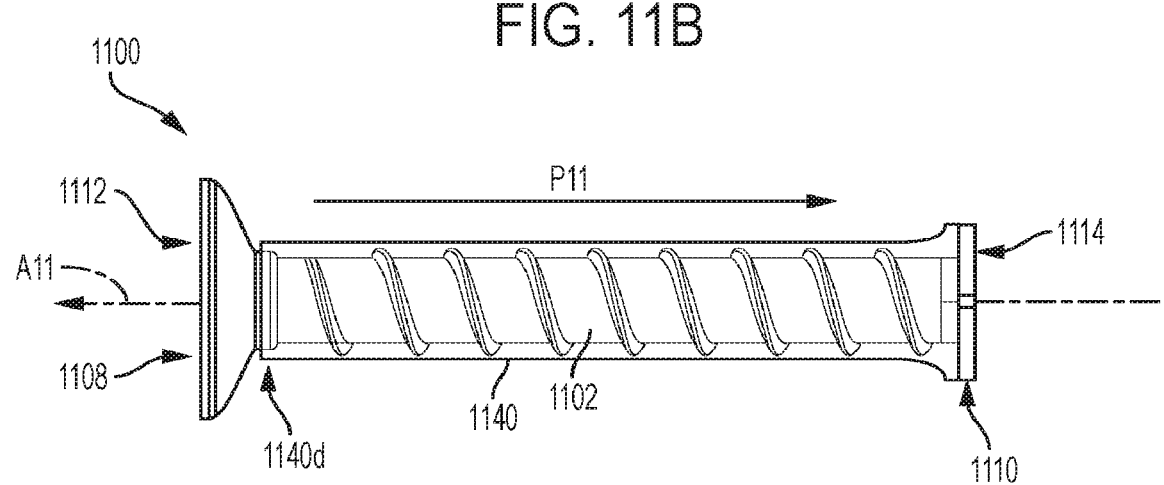
FIG. 11C is a side view of the cannula of FIG. 11B, where the flange is shown in a third position.

FIGS. 11A-11C illustrate a cannula 1100 having that is generally similar to cannulas 200, 300 (FIGS. 2 and 3), but it includes at least one adjustable flange. The cannula 1100 includes a body 1102 having a longitudinal axis A11, a first flange 1108, and a second flange 1110. The first and second flanges 1108, 1110 include first and second surfaces 1112, 1114, respectively, at least portions of which are reflective. Each of the first and second surfaces 1112, 1114 can be distal-facing or proximal-facing.

The first flange 1108 can be adjustable in various ways and, as shown by way of example, a suitable adjustment device can be used, such as a sheath 1140. FIG. 11A shows the cannula 1100 with the flange member 1108 in a first position. As shown in FIG. 11A, the sheath 1140 has an inner lumen that receives the body 1102 (partially obscured by the sheath 1140). The sheath 1140 extends over the flange member 1108 such that the flange member 1108 is disposed within the sheath 1140. The sheath 1140 can have any suitable configuration that allows it to move with respect to the longitudinal axis Al1 of the cannula's body 1102 so as to change a configuration of the flange 1108 to thereby change a configuration of the first surface 1112 of the flange 1108.

FIG. 11B shows the cannula 1100 with the flange member 1108 in a second position. As shown, in the second position, the sheath 1140 has been moved in a proximal direction P11 towards the second flange member 1110 of the cannula 1100. Moving the sheath 1140 in the proximal direction P11 causes the first flange member 1008 extend beyond a distal end 1140*d* of the sheath 1140 and expand radially outward.

FIG. 11C shows the flange member 1108 in a third position where the sheath 1140 is in a proximal-most position such that it abuts the second flange member 1110. In this configuration, the first flange member 1108 can be in a fully deployed configuration. However, it should be appreciated that the sheath 1140 can be configured such that the cannula 1100 can be used in a surgical procedure in the configuration shown in FIG. 11B, or in any of configurations that are intermediate between the configurations shown in FIG. 11A and 11C. In some embodiments, the sheath 1140 can be operated to cause the flange 1108 to have a configuration such that its reflective surface is substantially flat (as discussed, e.g., in connection with FIG. 9).

The sheath 1140 can be moveable with respect to the body 1102 of the cannula 1100 in various ways. For example, in some implementations, the body 1102 of the cannula 1100 can be threaded into the sheath 1140. In some embodiments, the first flange 1108 is flexible to accommodate deformation by the sheath 1140. In some embodiments, the flange 1108 can encompass multiple curved overlapping triangular or trapezoidal pieces that can be pivotally coupled to the body 1102 of the cannula 1100 such that the flange 1108 is able to expand radially outward as the sheath 1140 (or another device) is moved in the proximal direction P11. As mentioned above, the sheath 1140 can be removable.

In some embodiments, a configuration of a flange of a cannula can be adjusted using a suitable sliding adjustment device. The adjustment device can be attached to the surface of the flange, and it can be activated to change the shape of the flange member prior to inserting the cannula into a surgical portal. For example, the adjustment device can be configured to move between first and second configurations (and any intermediate configurations) in an umbrella-like manner. It should be appreciated, however, that the mechanism can be of any other suitable type.

Figure 12A:
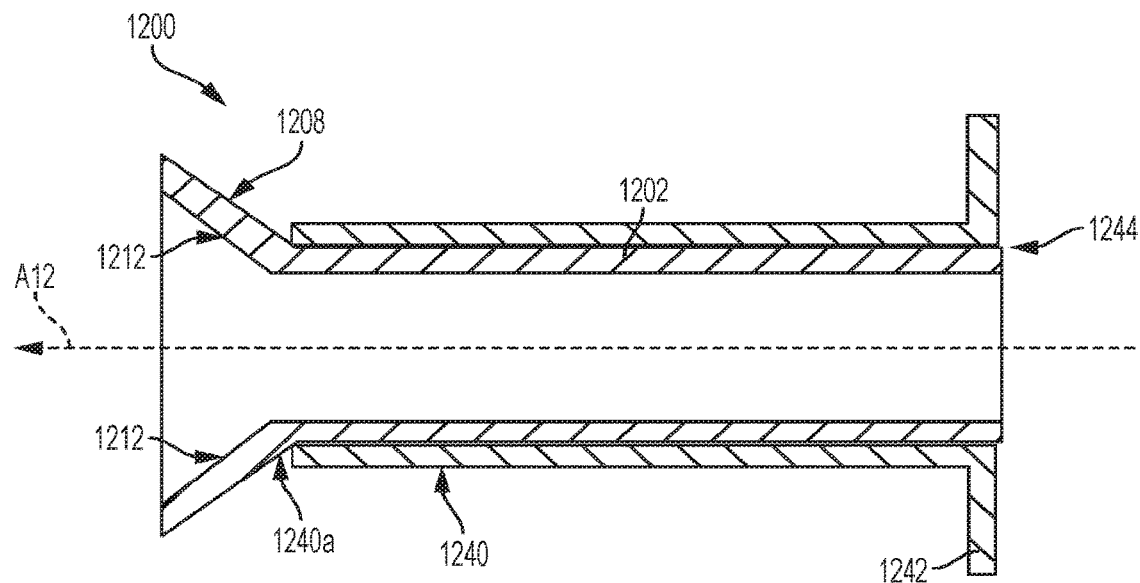
FIG. 12A is a side view of an exemplary embodiment of a cannula having an adjustable flange member, showing the flange member in a first configuration.
Figure 12B:
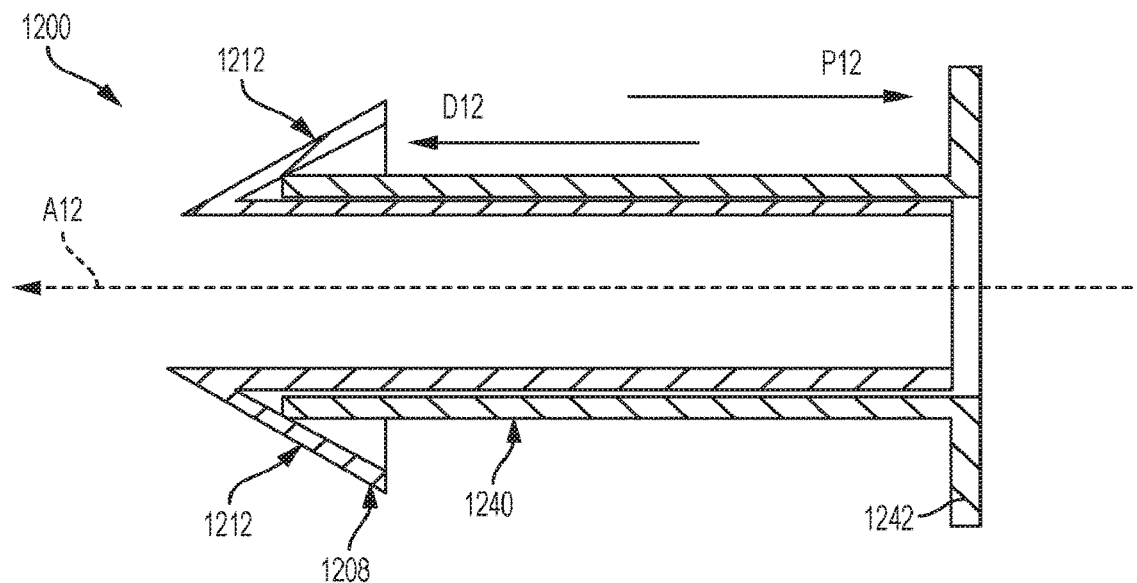
FIG. 12B is a side view of the cannula of FIG. 12A, showing the flange member in a second configuration.

In some embodiments, a sliding adjustment device can be in the form of a sheath coupled to a cannula's flange that is adjustable. FIGS. 12A and 12B show an embodiment of a cannula 1200 that includes a body 1202 having a longitudinal axis Al2, and a first adjustable flange 1208 that can be moved from a first configuration to a second configuration. As illustrated in FIG. 12A, the first flange 1208 has a first surface 1212, at least a portion of which is reflective. In this embodiment, an adjustment device is in the form of a sheath 1240 having a handle 1242 has an inner lumen 1244. As in the example shown in FIGS. 12A and 12B, the lumen 1244 of the sheath 1240 can have the cannula's body 1202 at least partially disposed therein.

As shown in FIG. 12A, a distal portion 1240*a* of the sheath 1240 is coupled to the flange member 1208, and the body 1202 of the cannula 1200 is slidably disposed within the lumen 1244 of the sheath 1240. The sheath 1240 can be coupled to the flange member 1208 in any suitable manner (e.g., using attachment feature(s)). In some embodiments, the sheath 1240 can be removably coupled to the flange member 1208 such that the use of the sheath 1240 may be optional.

When the flange 1208, which can be flexible, is in the first configuration, as shown in FIG. 12A, the first surface 1212 of the flange 1208 is in an inward-facing orientation. In use, the sheath 1240 is moved (e.g., by moving the handle 1242, or in other ways) in a proximal direction P12 relative to the body 1202 of the cannula 1200, which causes the flange 1208 to invert such that it moves from the first configuration to the second configuration, as shown in FIG. 12B. When the flange member 1208 is in the second configuration, the first surface 1212 is in an outward-facing configuration. In the illustrated embodiment, in the first configuration shown in FIG. 12A, the first surface 1212 of the flange 1208 is concave, and in the second configuration shown in FIG. 12B, the first surface 1212 of the flange 1208 is convex.

The sheath 1240 can be configured such that, during a surgical procedure, its proximal portion can be disposed outside the joint, such that the surgeon can manipulate the sheath 1240 to adjust the configuration of the flange member 1208 as desired. In this way, the shape of the flange's reflective surface is changed, which allows changing a viewing direction.

It should be appreciated that the sheath 1240 can be configured to be moved to any suitable distance to thereby cause the flange 1208 to move. Also, the flange 1208 can be adjusted such that it at least partially returns to the first configuration (e.g., the concave configuration of the surface 1212) by moving the sheath 1240 in a distal direction D12 (shown in FIG. 12B) relative to the body 1202 of the cannula 1200. The geometry of the first and second configurations of the flange 1208 can depend on the materials used to make the flange, equilibrium geometry of the flange 1208, configuration of the sheath 1240, and other factors. This embodiment can allow a surgeon to effectively adjust the configuration of the flange 1208 as desired.

It should be appreciated that a flange of a cannula can have various configurations that be moved between configurations in various ways. For example, although in the example shown in FIGS. 12A and 12B the sheath 1240 can be coupled to the body 1202 of the cannula 1200, in some embodiments, a convex configuration of a flange, such as the configuration of the flange 1208 shown in FIG. 12B, can be an original or default configuration. Thus, an adjustment device, such as the sheath 1240 or another device, can be used to move the flange between a concave configuration and the original convex configuration.

In some embodiments, a diameter of at least one portion of a body of the cannula can vary along the body's longitudinal axis. For example, a body of a cannula can include repeating surface features that are different from a thread. The features can facilitate securing a position of the cannula within tissue. Also, such a configuration of the cannula can allow "zooming" the cannula to obtain a desired view, such as by pushing and pulling the cannula into the joint space. In other words, in some implementations, the cannula can move between a configuration in which it is at least partially compressed and a configuration in which it is less compressed.

Figure 13:
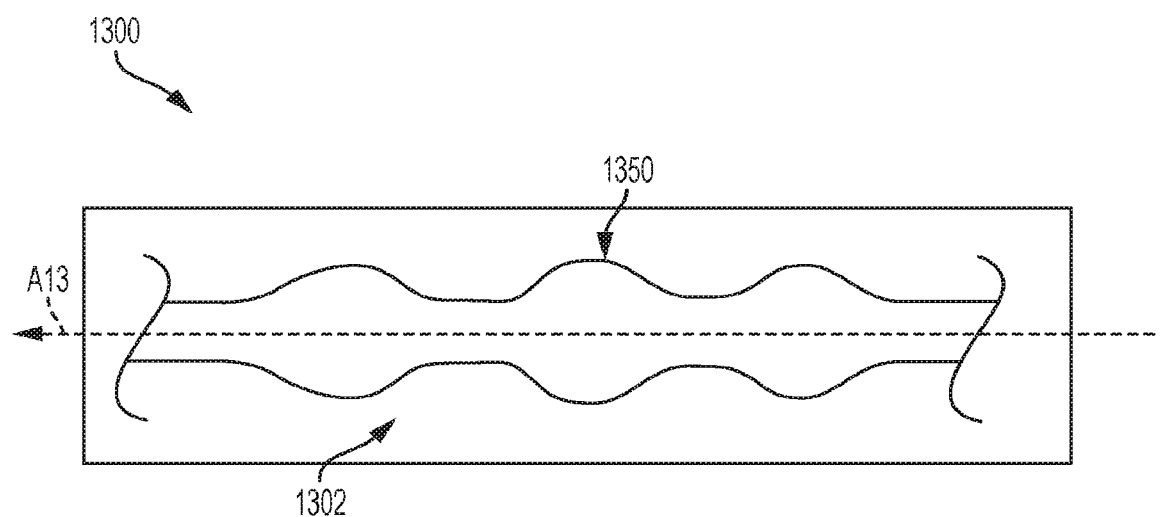
FIG. 13 is a side view of an embodiment of a cannula, showing at least one portion of the cannula having a varied diameter.

FIG. 13 shows an example of a cannula 1300 that has a body 1302 having a longitudinal axis A13. As shown, in this embodiment, the body 1302 has repeating surface features such as protrusions 1350. In this example, the surface protrusions 1350 are generally semi-circular, such that the body 1302 of the cannula 1300 generally has a repeating hourglass shape. The entire body 1302 or one or more portions thereof can be made reflective. It should be appreciated that the protrusions can have any other shapes and they can be formed in any manner. Also, any number of protrusions or other surface feature (e.g., bumps, ribs, etc.) can be formed that can facilitate securing a position of the cannula within tissue. The surface protrusions 1350 can vary in size and need not be symmetrical with respect to the body 1302 of the cannula 1300. In some embodiments, a body 1302 of the cannula 1300 can include portions, or sections, that that can extend radially outward from the longitudinal axis A13. For example, the cannula 1300 can have flanges, which can be configured similar to any flanges described herein.

In the embodiments described above, one or more of various portions of a surgical cannula can have a reflective surface. It should be appreciated that other surgical instruments can have reflective surface(s) in accordance with the described techniques. For example, a surgical sled, which can be used to guide tools to a surgical site during a surgical procedure, such as arthroscopic surgery, can have one or more reflective surfaces. A surgical sled having a reflective surface in accordance with the described techniques can be used to access a joint, such as, for example, a knee, shoulder, or another joint. In some cases, in which a sled is used, an incision smaller than that that would be required to access a surgical site with a cannula can be created. The sled can be used to navigate around a joint, through tendons, muscle, joint capsule, or any other areas percutaneously as a result of having a relatively small physical profile. Also, the sled can be removed from and reintroduced into a surgical site a number of times, with a decreased risk of injuring a patient.

Figure 14A:
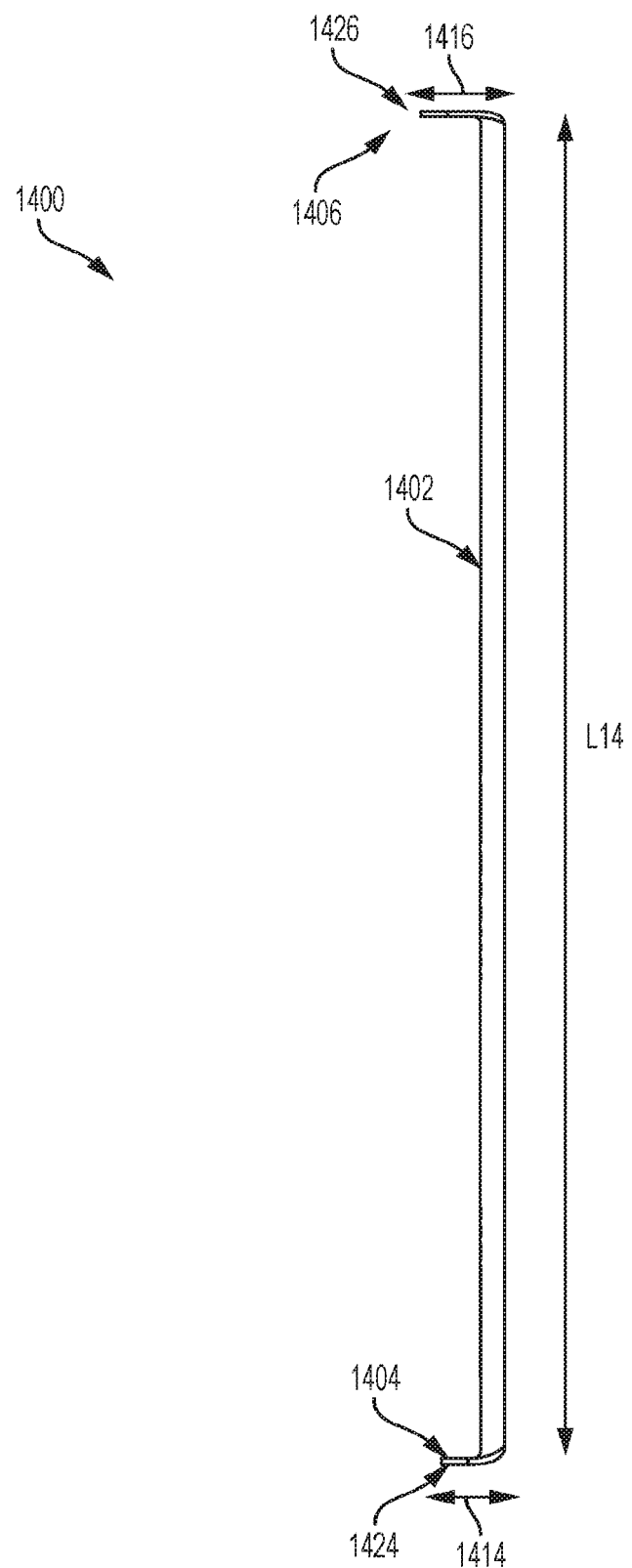
FIG. 14A is a perspective side longitudinal view of an embodiment of a surgical sled.
Figure 14B:
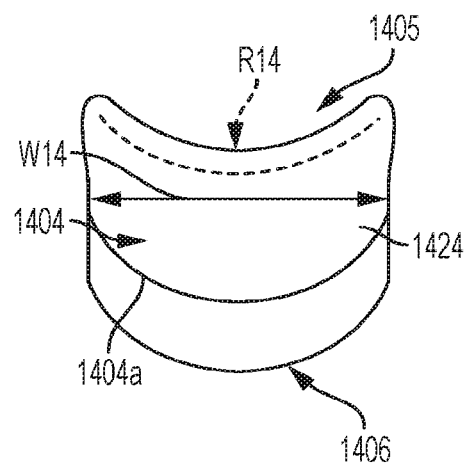
FIG. 14B is an end view of the surgical sled of FIG. 14A.
Figure 14C:
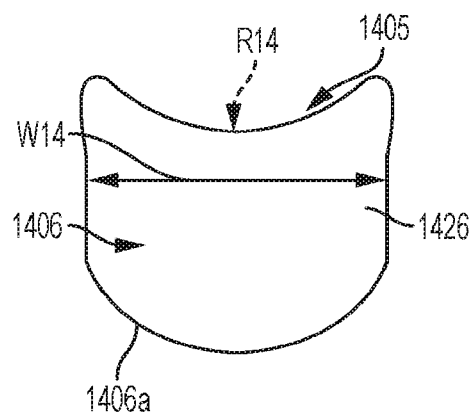
FIG. 14C is another end view of the opposed end of the surgical sled of FIG. 14A.

FIGS. 14A-14C show an exemplary embodiment of a surgical sled 1400 that can be used to guide tools to a surgical site. As shown in FIG. 14A, the sled 1400 has an elongate body 1402 having a longitudinal axis L14. The sled 1400 also has first and second end features 1404, 1406 extending from opposed ends of the body 1402 in the same direction relative to the body 1402. The end features 1404, 1406 are formed approximately perpendicular to the longitudinal axis L14 of the sled's body 1402, though they can be slightly curved or angled other than being perpendicular, as discussed below.

The surgical sled 1400 can have various configurations. In this example, the elongate body 1402 is relatively thin. As shown in FIGS. 14B and 14C, the body 1402 is slightly curved along its length and has a radius of curvature R14. Thus, as shown in FIGS. 14B and 14C, a side 1405 of the body 1402 is slightly concave such that the body 1402 is partially semi-circular in cross-section taken perpendicular to the longitudinal axis L14 thereof. The end features 1404, 1406 are slightly curved towards each other and away from the side 1405 of the body 1402 having the slightly concave configuration. In particular, first and second outer surfaces 1424, 1426 of the first and second end features 1404, 1406, respectively, are slightly curved towards one another.

The end features 1404, 1406 have different respective lengths. For example, in this embodiment, the second end feature 1406 can have a greater length 1416 than a length 1414 of the first end feature 1404. The end features 1404, 1406 can have rounded ends 1404a, 1406a, to minimize tissue damage in use.

The surgical sled 1400 can have various dimensions. For example, although the body 1402 can have any suitable length, in at least one embodiment, the length of the body 1402 is about 7 inches. The body 1402 is longer than the end features. For example, in at least one embodiment, the length of the second end feature 1406 is approximately 0.32 inches, and the length of the first end feature 1404 is approximately 0.24 inches. However, it should be appreciated that the body and the end features of the sled can have any other suitable lengths. For example, in various implementations, the length of the body can range from about 2 inches to about 14 inches, and the length of the end features can range from about 0.1 inches to about 0.38 inches.

The body 1402 and the end features 1404, 1406 have a width (W14 in FIGS. 14B and 14C) that generally corresponds to a width of an incision to be made in a patient's body during an arthroscopic surgical procedure. In some embodiments, the sled 1400 can be part of a kit including sleds of different widths, for accessing surgical sites through incisions of corresponding different widths (or diameters). In this example, the body 1402 and the end features 1404, 1406 have the same width that does not vary along their lengths. In some embodiments, however, the width W14 varies along the length of the sled's body. Also, the radius of curvature R14 of the sled's body may vary along the length of the body.

For reasons similar to those described above with regard to various cannulas, it is desirable for the sled 1400 to have one or more reflective surfaces that a surgeon can use to view a surgical site from various angles. The sled 1400 can be highly reflective in specific locations to aid a surgeon in enhanced visualization while using an arthroscope. The reflective portions can potentially allow the surgeon to view around corners and/or in other areas that would not otherwise be visible. Accordingly, the outer surfaces 1424, 1426 of the first and second end features 1404, 1406, respectively, can have one or more reflective portions. In the illustrated example, the entire surfaces 1424, 1426 of the first and second end features 1404, 1406 are made reflective.

The sled 1400 can be made of various materials and portion(s) of the sled can be made reflective in various ways. The sled 1400 can be made, for example, from stainless steel, polycarbonate, or any other suitable material. In some embodiments, the end features 1404, 1406 can be rigid or semi-rigid, and one or more areas of the outer surfaces 1424, 1426 can be polished to made them reflective. The first and second surfaces 1424, 1426 can be highly polished (mechanically or electrically) such that they can form images of objects and other elements reflected in them. Thus, in this example, the first and second surfaces 1424, 1426 are polished to a mirror finish to provide high reflectivity.

In other embodiments, the surfaces 1424, 1426 of the end features 1404, 1406 can have one or more reflective portions incorporated therein via an over-molding process. In some embodiments, the end features 1404, 1406 can be formed from a soft flexible material that can be metallized (e.g., using an over-molding, vapor deposition, or another process) to make at least a portion of each of the first and second surfaces 1412, 1414 reflective.

In use, the sled 1400 can be inserted through a surgical access portal until one of the end features 1404, 1406 is at the surgical site. Another surgical instrument such as, e.g., a shaver or drill bit, can then be inserted into the access portal and guided along the body 1402 of the sled 1400 to the surgical site.

It should be appreciated that the surgical sled having at least a portion thereof reflective can have numerous variations. For example, only one of end features can be made entirely or partially reflective. The end features can be formed integrally with the sled's body. However, in some embodiments, the end features can be separate elements coupled to the sled's body in a suitable manner. As another variation, in some embodiments, one or both of the end features of a surgical sled having a reflective surface can be at least partially flexible. A configuration of a partially flexible end feature can be adjustable. For example, an adjustment device, such as a device having a suitable hinge mechanism, may be used to adjust a configuration of an end feature.

Figure 15:
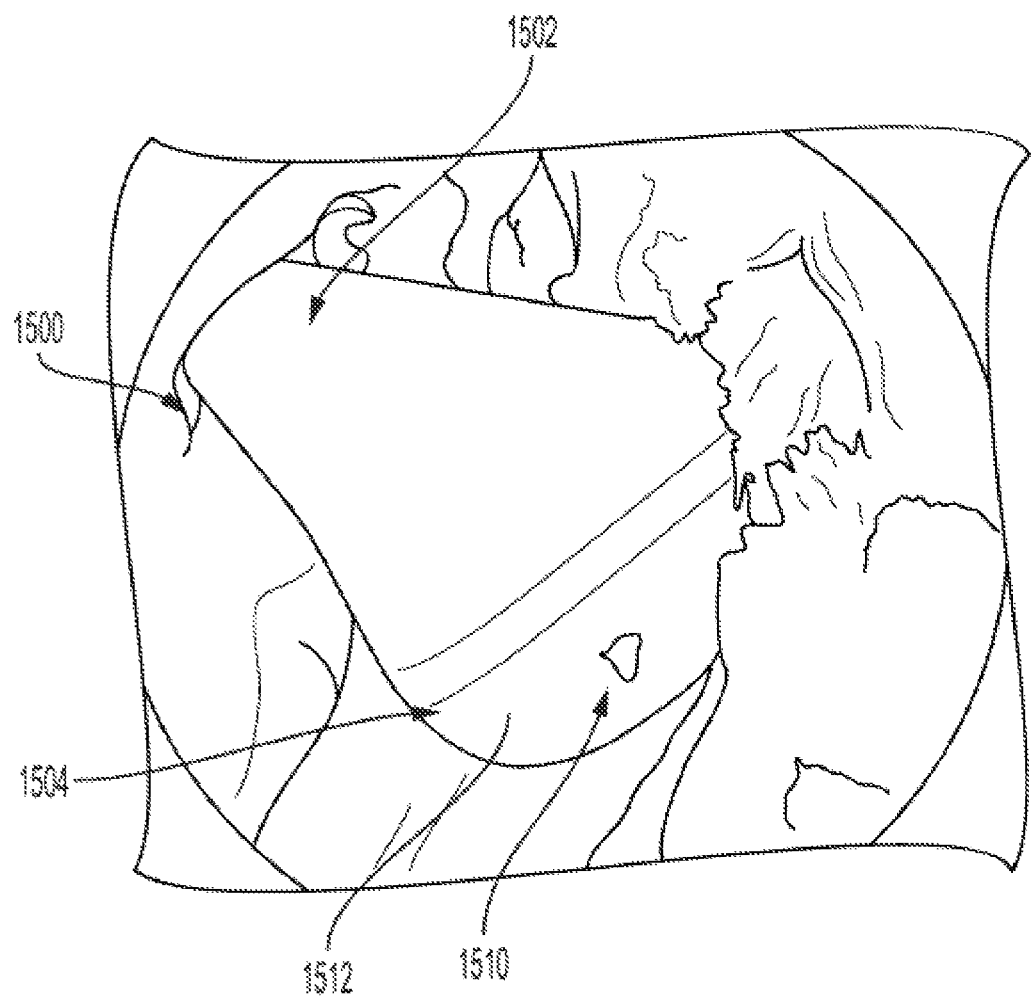
FIG. 15 is an image of an embodiment of a surgical sled inserted to a surgical site.

FIG. 15 is an image illustrating a field of view of an imaging instrument, such as an arthroscope, during a surgical procedure, where the arthroscope has been inserted through a first portal in a patient's body, and a sled 1500 has been inserted through a second portal in the patient's body. The sled 1500 can generally be similar to sled 1400 (FIGS. 14A-14C) and it includes a body 1502 and a first end feature 1504. The sled 1500 can also include a second end feature (not shown). The first end feature 1504 can include a surface 1512 (e.g., similar to any of sled's outer surfaces 1424, 1426 in FIGS. 14A-14C), wherein at least a portion of the surface 1512 is reflective. As shown in FIG. 15, the sled 1500 is advanced to the surgical site such that the end feature 1504 is disposed within the surgical site. A reflection 1510 of a drilled hole is visible in the reflective surface 1512 of the end feature 1504. The drilled hole may otherwise not be in the field of view of the arthroscope, and the ability to view the reflection 1510 of the hole facilitates insertion of an implant into the hole.

The current subject matter provides technical advantages of working with a cannula, a sled, or another surgical instrument having at least one reflective surface that can be used to improve visibility of a surgical site, without introducing additional devices into the surgical site.

A person skilled in the art will appreciate that the devices, systems, and methods disclosed herein have application in conventional minimally-invasive and open surgical instrumentation as well application in robotic-assisted surgery. In some embodiments, the devices, systems, and methods described herein are provided for open surgical procedures, and in other embodiments, the devices, systems, and methods are provided for arthroscopic, laparoscopic, endoscopic, and other minimally invasive surgical procedures. The devices may be fired directly by a human user or remotely under the direct control of a robot or similar manipulation tool. However, a person skilled in the art will appreciate that the various methods, systems, and devices disclosed herein can be used in numerous surgical procedures and applications. Those skilled in the art will further appreciate that the various instruments disclosed herein can be inserted into a body in any way, such as through a natural orifice, through an incision or puncture hole formed in tissue, or through an access device, such as a trocar cannula. For example, the working portions or end effector portions of the instruments can be inserted directly into a patient's body or can be inserted through an access device that has a working channel through which the end effector and elongated shaft of a surgical instrument can be advanced.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A cannula, comprising:
   an elongate body extending along a longitudinal axis, the elongate body having a proximal end, a distal end, and a lumen extending through the elongate body between openings at the proximal and distal ends; and
   a first flange member that extends at least partially around at least one of the openings, the first flange member having a first surface, wherein at least a portion of the first surface is reflective;
   wherein an angle at which the first flange member is oriented relative to the longitudinal axis of the elongate body is adjustable; and
   wherein the angle is adjustable using an adjustment device having an inner lumen that is configured to receive the elongate body therein, and, with the elongate body configured to extend through tissue such that the proximal end of the elongate body is on a first side of the tissue and the distal end of the elongate body is on a second side of the tissue, the adjustment device is configured to move along the longitudinal axis of the elongate body such that engagement of the adjustment device with the first flange member causes the angle to be adjusted.

2. The cannula of claim 1, further comprising the adjustment device;
   wherein the adjustment device comprises a sheath coupled to the first flange member such that when the sheath slides longitudinally in a proximal direction relative to the first flange member, the first flange member is configured to move from a concave configuration to a convex configuration.

3. The cannula of claim 2, wherein the first flange member is configured to move automatically from the concave configuration to the convex configuration.

4. The cannula of claim 1, further comprising the adjustment device;
   wherein the adjustment device comprises a sheath coupled to the first flange member such that when the sheath is moved in a proximal direction, at least the portion of the first surface that is reflective is configured to move from being inward facing to being outward facing.

5. The cannula of claim 1, wherein the angle is adjustable such that the first flange member is configured to move between a first configuration and a second configuration.

6. The cannula of claim 5, wherein with the first flange member in the first configuration, at least the portion of the first surface that is reflective is inward facing; and
   with the first flange member in the second configuration, at least the portion of the first surface that is reflective is outward facing.

7. The cannula of claim 5, further comprising the adjustment device;

wherein the adjustment device comprises a sheath coupled to the first flange member such that when the sheath is moved longitudinally in a proximal direction relative to the first flange member, the first flange member is configured to move from the first configuration to the second configuration.

8. The cannula of claim 1, wherein an outer wall of the elongate body has at least one thread formed thereon.

9. The cannula of claim 1, wherein a thin flexible member on the first flange member provides the reflectivity of the first surface.

10. The cannula of claim 1, wherein a mirror on the first flange member provides the reflectivity of the first surface.

11. The cannula of claim 1, wherein a reflective material painted on the first flange member provides the reflectivity of the first surface.

12. A surgical method, comprising:
advancing a cannula through a first portal to a target site in a patient's body, the cannula comprising:
an elongate body extending along a longitudinal axis, the elongate body having a proximal end, a distal end, and a lumen extending through the elongate body between openings at the proximal and distal ends, and
a first flange member that extends at least partially around at least one of the oepnings, the first flange member having a first surface, wherein at least a portion of the first surface is reflective, and wherein an angle at which the first flange member is oriented relative to the longitudinal axis of the elongate body is adjustable;
advancing an imaging device comprising at least one image sensor through a second portal towards the target site;
performing a surgical function at the target site; and
viewing a result of the surgical function with the imaging device by directing the imaging device at at least the portion of the first surface of the cannula that is reflective such that at least the portion of the first surface that is reflective displays a reflected image of the result of the surgical function at the target site.

13. The method of claim 12, wherein the first portal comprises one of an anterior portal and a posterior portal, and the second portal comprises another one of the anterior portal and the posterior portal.

14. The method of claim 12, wherein performing the surgical function at the target site comprises forming a hole in a bone.

15. The method of claim 12, wherein the at least the portion of the first surface that is reflective has one of:
a thin flexible member thereon;
a mirror thereon; and
a reflective material painted thereon.

* * * * *